(12) United States Patent
Kumar

(10) Patent No.: US 6,283,752 B1
(45) Date of Patent: Sep. 4, 2001

(54) UNIVERSAL IMPRESSION COPING SYSTEM

(75) Inventor: Ajay Kumar, Palmdale, CA (US)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/352,229

(22) Filed: Jul. 13, 1999

Related U.S. Application Data

(60) Provisional application No. 60/128,356, filed on Apr. 8, 1999, provisional application No. 60/097,787, filed on Aug. 25, 1998, and provisional application No. 60/092,597, filed on Jul. 13, 1998.

(51) Int. Cl.[7] .................................................. A61C 13/12
(52) U.S. Cl. ............................................ 433/172; 433/214
(58) Field of Search .................................. 433/213, 214, 433/172, 173, 174

(56) References Cited

U.S. PATENT DOCUMENTS

| | | |
|---|---|---|
| 4,431,416 | 2/1984 | Niznick . |
| 4,955,811 | 9/1990 | Lazzara et al. . |
| 5,052,929 | 10/1991 | Seal . |
| 5,055,047 | 10/1991 | Names . |
| 5,078,606 | 1/1992 | Söderberg . |
| 5,098,294 | 3/1992 | Lee et al. . |
| 5,106,300 * | 4/1992 | Voitik ................................ 433/173 |
| 5,125,839 | 6/1992 | Ingber et al. . |
| 5,125,841 | 6/1992 | Carlsson et al. . |
| 5,213,502 | 5/1993 | Daftary . |
| 5,312,253 | 5/1994 | Chalifoux . |
| 5,312,254 | 5/1994 | Rosenlicht . |
| 5,316,477 * | 5/1994 | Calderon ............................ 433/172 |
| 5,328,371 | 7/1994 | Hund et al. . |
| 5,334,024 | 8/1994 | Niznick . |
| 5,350,297 | 9/1994 | Cohen . |
| 5,538,426 * | 7/1996 | Harding et al. .................... 433/214 |
| 5,549,475 | 8/1996 | Duerr et al. . |
| 5,584,694 | 12/1996 | Forsmalm et al. . |
| 5,658,147 * | 8/1997 | Phimmasone ...................... 433/214 |
| 5,662,476 | 9/1997 | Ingber et al. . |
| 5,674,073 | 10/1997 | Ingber et al. . |
| 5,685,714 | 11/1997 | Beaty et al. . |
| 5,685,715 | 11/1997 | Beaty et al. . |
| 5,725,375 | 3/1998 | Rogers . |
| 5,733,122 | 3/1998 | Gordon . |
| 5,829,981 | 11/1998 | Ziegler . |
| 5,846,079 | 12/1998 | Knode . |
| 5,899,695 | 5/1999 | Lazzara et al. . |
| 5,904,483 | 5/1999 | Wade . |
| 5,938,443 | 8/1999 | Lazzara et al. . |
| 6,045,361 | 4/2000 | Misch et al. . |

FOREIGN PATENT DOCUMENTS 2667499   4/1992   (FR) .

* cited by examiner

Primary Examiner—Todd E. Manahan
(74) Attorney, Agent, or Firm—Knobbe, Martens, Olson & Bear, LLP

(57) ABSTRACT

A universal impression coping system and impression coping assembly is provided for taking dental impressions of a dental restoration site and which me be used efficaciously for both open- and closed-tray impression techniques. An inexpensive transfer impression pin and coping assembly is further provided having registration means providing unique orientation of the transfer coping and visual and tactile feedback for assuring accurate dental impressions using the closed tray impression technique.

38 Claims, 20 Drawing Sheets

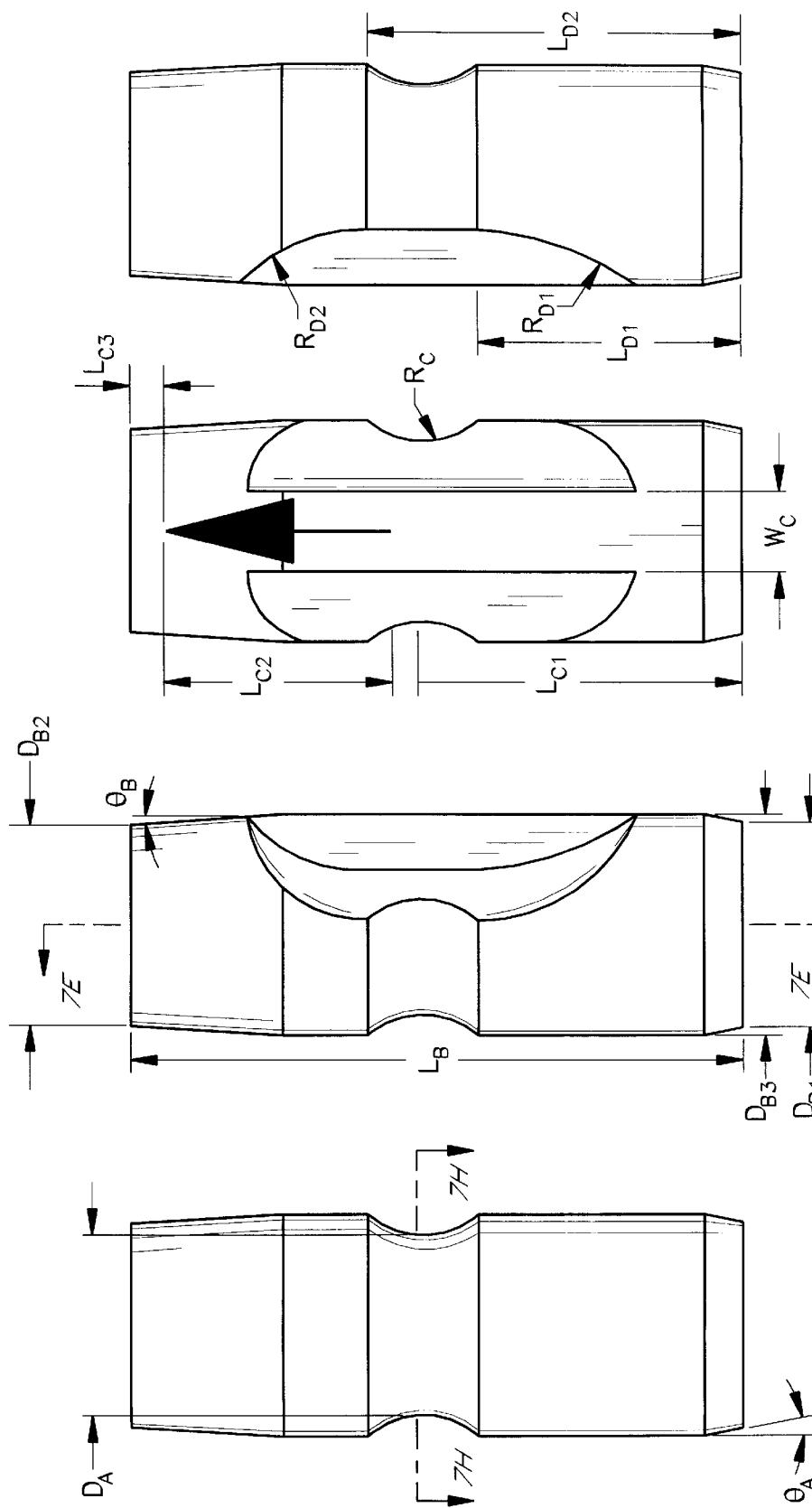

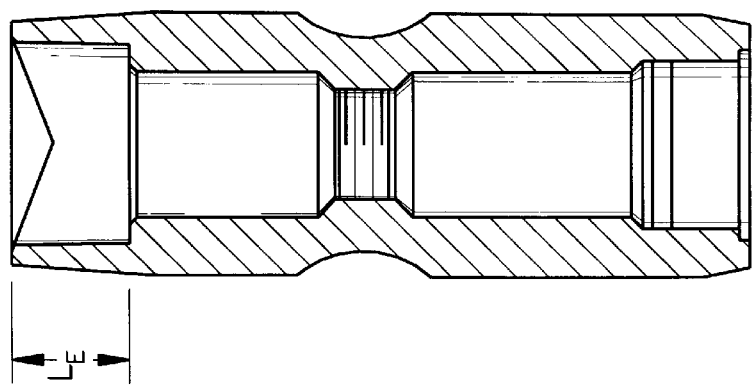
FIG. 7E
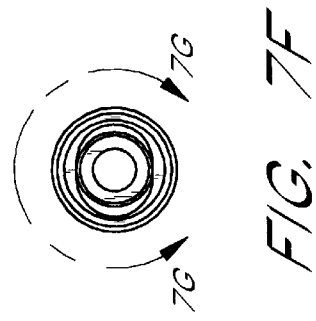
FIG. 7F
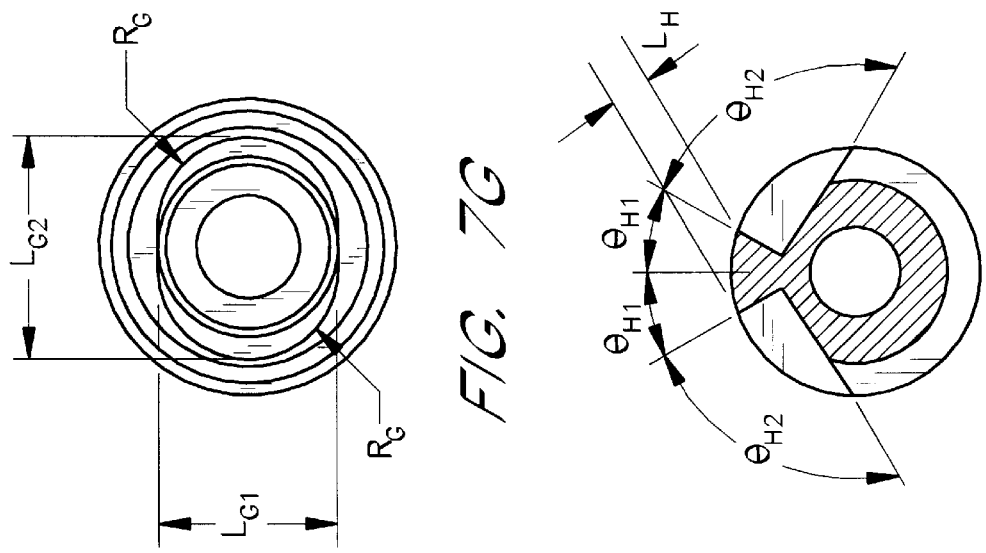
FIG. 7G
FIG. 7H

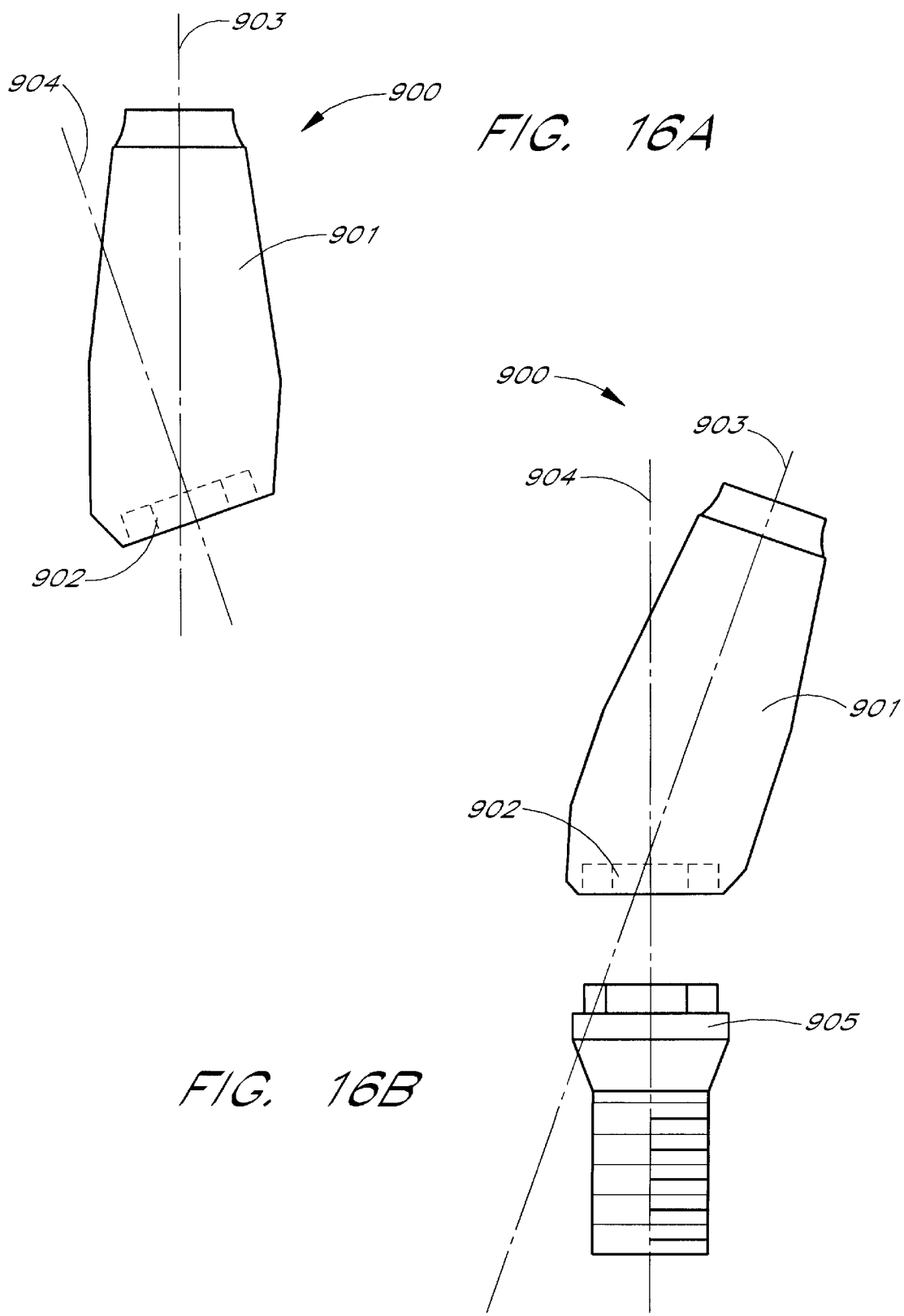

UNIVERSAL IMPRESSION COPING SYSTEM

RELATED APPLICATIONS

This application claims the benefit of U.S. Provisional Application No. 60/092,597, filed Jul. 13, 1998, U.S. Provisional Application No. 60/097,787, filed Aug. 25, 1998, and U.S. Provisional Application No. 60/128,356, filed Apr. 8, 1999.

BACKGROUND OF THE INVENTION

1. Field of the Invention

This invention relates to dental impression copings of the type used in implant dentistry to take impressions of a dental implant site from which accurate models can be constructed. More particularly, the invention relates to a universal impression coping system and method for taking accurate dental impressions using either open-tray or closed-tray techniques.

2. Description of the Related Art

Implant dentistry involves the restoration of one or more teeth in a patient's mouth using artificial components, including typically an implant fixture or root and a prosthetic tooth and/or final abutment which is secured to the implant fixture. According to state of the art techniques, the process for restoring a tooth and its root is carried out generally in three stages.

Stage I involves implanting the dental implant fixture into the bone of a patient's jaw. The oral surgeon first accesses the patient's jawbone through the patient's gum tissue and removes any remains of the tooth to be replaced. Next, the specific site in the patient's jaw where the implant will be anchored is widened by drilling and/or reaming to accommodate the width of the dental implant fixture to be implanted. Then, the dental implant fixture is inserted into the hole in the jawbone, typically by screwing, although other techniques are known for introducing the implant in the jawbone.

The implant fixture itself is typically fabricated from pure titanium or a titanium alloy. Such materials are known to produce osseointegration of the fixture with the patient's jawbone. The dental implant fixture also typically includes a hollow threaded bore through at least a portion of its body and extending out through its proximal end which is exposed through the crestal bone for receiving and supporting the final tooth prosthesis and/or various intermediate components or attachments.

After the implant is initially installed in the jawbone a temporary healing cap is secured over the exposed proximal end in order to seal the internal bore. The patient's gums are then sutured over the implant to allow the implant site to heal and to allow desired osseointegration to occur. Complete osseointegration typically takes anywhere from four to ten months.

During stage II, the surgeon reassesses the implant fixture by making an incision through the patient's gum tissues. The healing cap is then removed, exposing the proximal end of the implant. A mold or impression is then taken of the patient's mouth to accurately record the position and orientation of the implant within the mouth. This is used to create a plaster model or analogue of the mouth and/or the implant site and provides the information needed to fabricate the prosthetic replacement tooth and any required intermediate prosthetic components. Stage II is typically completed by attaching to the implant a temporary healing abutment or other transmucosal component to control the healing and growth of the patient's gum tissue around the implant site.

Stage III involves fabricating and placement of a cosmetic tooth prosthesis to the implant fixture. The plaster analogue provides laboratory technicians with a model of the patient's mouth, including the orientation of the implant fixture relative to the surrounding teeth. Based on this model, the technician constructs a final restoration. The final step in the restorative process is replacing the temporary healing abutment with the final restoration.

To achieve optimal results in terms of overall aesthetics and bio-functioning ability of the tooth restoration, it is essential in stage II that the plaster analogue accurately reflect the true position and orientation of the implant in the patient's mouth and that in stage III such position and orientation is faithfully replicated when securing the final tooth restoration to the implant. To help achieve this accuracy and faithful replication, one or more indexing means are typically provided on the proximal end of the implant and corresponding mating indexing means are formed on the various mating components which are adapted to be fitted to the implant. Such indexing means provide desired orientation of the implant and mating components relative to one another and also prevent undesired rotation.

Such indexing means frequently take the form of a hexagonal boss or recess ("hex") formed on the proximal portion of the implant exposed through the crestal bone. For externally threaded implants the hex may also be used to engage a driving tool for driving the implant into an internally threaded bore or osteotomy prepared in the patient's jawbone (mandible or maxilla). When the implant is filly installed in a patient's jawbone the hex or other indexing means is typically exposed through the crestal bone so that accurate indexing may be provided between the implant and the final prosthesis and/or various intermediate mating prosthetic components.

As noted above, during stage II of the dental restorative process a mold or impression is taken of the patient's mouth to accurately record the position(s) and orientation(s) of the indexing means within the mouth at the implant site(s) and to thereby provide the information needed to fabricate the restorative replacement(s) and/or intermediate prosthetic components. According to the state of the art, this is done using a casting or impression material formed of a soft resin—typically polyvinylsiloxane or polyether—which can be applied over the implant site using a suitable impression tray and allowed to cure in situ. The impression material is sufficiently resilient such that it can be removed from the patient's mouth after it is cured (or partially cured) while at the same time retaining an accurate impression of the patient's mouth and particularly the implant site.

However, because the indexing means of the implant is typically quite small and may be recessed partially beneath the gums of a patient, a secondary or intermediate impression element is typically used to help transfer accurately the orientation of the indexing means of the implant. This intermediate impression element is commonly called a "coping" or "impression coping." Examples of impression copings as found in the prior art are shown in U.S. Pat. No. 4,955,811 to Lazzara et al., e.g. FIGS. 5, 6, and 9. There are primarily two types of such impression copings used today—so-called "transfer" impression copings and so-called "pick-up" impression copings.

Conventional transfer impression copings have an impression portion adapted to form a unique or indexed impression in the impression material and a base portion having mating indexing means adapted to mate with the exposed indexing means of the implant. In use, the impression coping is temporarily secured to the exposed proximal end of the implant fixture such that the mating indexing means of the impression coping and implant are interlockingly mated to one another. Typically, a threaded screw or bolt is used to temporarily secure the impression coping to the implant fixture.

Once the impression coping(s) is secured to the implant fixture(s), an impression of the coping(s) relative to the surrounding teeth is taken. A U-shaped tray filled with an impression material is placed in the patient's mouth over the implant site. The patient bites down on the tray, squeezing the impression material into the implant site and around the impression coping(s). Within a few minutes, the impression material cures or hardens to a flexible, resilient consistency. The impression tray is then removed from the patient's mouth to reveal an impression of the implant site and the impression coping(s). The restorative dentist then removes the impression coping(s) from the patient's mouth and transfers the coping(s) back into the impression material, being careful to preserve the proper orientation of the indexing means. This impression method using transfer impression copings is commonly referred to as the "closed-tray" technique.

Conventional pick-up impression copings are similar to transfer copings described above, except that pick-up impression copings typically include an embedment portion adapted to non-removably embed the impression coping securely within the impression material. In this case, once the impression is taken the tray is removed from the patient's mouth. The impression coping(s) remain in the impression material and are "picked up" and pulled away from the patient's mouth along with the impression material. To facilitate such pick-up removal of impression copings, the tray is provided with one or more apertures or openings through which a tool may be inserted to loosen the screw or bolt securing each coping. Thus, this impression technique is commonly referred to as the "open-tray" technique.

The choice of which technique to use (open tray vs. closed tray) is based primarily on individual patient characteristics and the clinician's preference. While the closed-tray technique is somewhat simpler in its design and execution, it is sometimes prone to inaccuracies where sufficient care is not taken during the step of reinserting the impression coping(s) into the impression material. While the open-tray technique is generally more accurate, it is more complex and, as a result, often takes more time to prepare and execute. In terms of patient indications, the open-tray technique is particularly well suited for multi-site dental restoration procedures, especially when the divergence angle between multiple adjacent implants is, for example, greater than 30°, or when the dentist wishes to utilize a verification stent to check the accuracy of the working stone model.

Conventionally, open- and closed-tray systems have required different impression copings to be used with each technique. In the closed-tray system, the restorative dentist must be able to remove the tray and the impression material from the transfer impression coping and screw assembly such that the impression coping remains in the patient's mouth after the impression material is removed. As a result, transfer impression copings used for the closed-tray technique tend to be conical or tapered in shape, with the smaller diameter located at the coronal aspect of the coping, and the larger diameter located at the base, or apical aspect, of the coping where the coping connects to the abutment and implant assembly. This conical shape or taper facilitates removal of the impression material while the coping assembly remains in the patient's mouth.

In the open-tray system, the restorative dentist requires the impression copings to remain securely retained within the impression material as the impression tray is removed from the patient's mouth. As a result, pick-up impression copings used for the open-tray technique typically have a protuberant "lip" or similar embedment projection at their coronal aspect, such that the diameter of the lip is larger than the diameter of the immediately adjacent (more apical) area of the transfer coping. This allows for "grabbing" or traction of the impression material as it is being removed from the patient's mouth.

The practice of using different impression copings for open- and closed-tray systems significantly adds to the cost of restorative dentistry. Often, the prosthodontist does not make a final decision whether to use one technique or the other until after the patient is examined on the day of the restorative procedure. At that time a judgement call is made and the prosthodontist may decide to use either the closed-tray technique or open-tray technique depending upon the particular prevailing indications. For example, a particular prosthodontist may generally prefer to use the closed-tray technique, but may choose the open-tray technique for a given patient case because of excessive or irregular angulation of the longitudinal axes of the implants or adjacent teeth. The ability to make such clinical adjustments requires that clinicians have both open- and closed-tray systems on hand. But, maintaining separate inventories of both transfer and pick-up impression copings in the various sizes and types required for clinical use on a range of patients increases the carrying costs, overhead and administrative burdens of the restorative dentist.

Moreover, conventional transfer (closed tray) impression copings are expensive to manufacture and/or suffer from inaccuracies. A key aspect to achieving accurate impressions using the closed-tray technique is ensuring that the transfer impression coping is reinserted into the impression material in the correct orientation. Any inaccuracy in the angular orientation of the impression coping in the impression material will be transferred directly to the plaster analogue. Once the plaster analogue is cast, inaccuracies in the orientation of the impression coping will not be detected until after fabrication of the final restoration and its attempted placement in the patient's mouth.

Most modem transfer copings provide some form of registration means, such as a flat or the like, for helping the prosthodontist or dental technician identify the correct orientation of the transfer coping when reinserting it into the impression material. Nevertheless, even such improved transfer copings are still prone to occasional misorientation during reinsertion when sufficient care is not exercised or when the impression material is particularly soft.

An alternative approach provides a transfer impression coping having multiple registration means symmetrically arranged about a central axis. In this manner, no matter which way the coping is turned or rotated within the negative impression formed in the impression material the symmetry of the design will urge the coping into any one of a number of indexed orientations. See, e.g. U.S. Pat. No. 5,685,715 to Lazzara et. al. While this "self-indexing" coping design ensures a higher probability that an "indexed" orientation will be achieved, it does not necessarily increase the probability that the indexed orientation will faithfully reproduce the orientation of the implant. In particular, the self-indexing feature of these coping designs requires that precise symmetry and tolerances be maintained when machining the coping to ensure that each possible indexed orientation of the coping faithfully reproduces the desired implant orientation. As a result of the different possible indexed orientations, there is an increased risk that even relatively small inaccuracies in the matching of these small parts may create noticeable errors in the orientation of the final restoration. The tighter tolerances and demand for symmetry further increases the expense of manufacturing such self-indexing transfer impression copings.

SUMMARY OF THE INVENTION

Accordingly, it is a principle object and advantage of the present invention to overcome some or all of these limitations and to provide a universal impression coping system which is relatively inexpensive to manufacture and which may be used efficaciously for both open- and closed-tray impression techniques to obtain accurate dental impressions for restorative dental procedures.

In accordance with one embodiment the present invention provides a system of components for, and a method of, fabricating a prosthodontic restoration which can be fixed non-rotationally on a dental implant fixture of the kind having a threaded socket together with anti-rotation means to restrain components non-rotationally attached to the fixture. This system utilizes a single transfer coping that is adapted to be used in both open- and closed-tray systems. In the open-tray configuration the present invention provides a pick-up coping fitted with an open-tray screw and an impression-coping cap. The impression-coping cap facilitates maintenance of the position of the transfer coping within the impression material used by the dentist to make an impression of the patient's case. In the closed-tray configuration of the present invention, the universal impression coping is fitted with a closed-tray screw cap. The shape of the transfer coping, with the closed-tray screw threaded therein, facilitates removal of the impression material from the patient's case, while the impression coping remains anchored to the patient's dental implant and/or abutment.

In accordance with another embodiment the present invention provides a universal impression coping system for use in taking an accurate dental impression of an implant installed in a patient's jawbone using either a closed-tray or open-tray impression technique. The system includes an impression pin, including a body portion having a proximal end and a distal end. The proximal end is configured and adapted to be secured to the implant and further comprises an indexing boss or recess formed therein for interlockingly engaging a corresponding mating indexing boss or recess formed on the implant. The impression pin also has a central bore extending substantially completely through the impression pin and opening through the proximal and distal ends. A cap screw is provided having a cap portion and a threaded shaft portion. The threaded shaft portion is adapted to pass through the bore extending through the impression pin and to threadingly engage a threaded bore of the implant. The cap portion is further adapted to selectively matingly engage or abut against the distal end of the impression pin. An embedment cap is also provided having one or more impression gripping elements. The embedment cap is adapted to selectively matingly engage or abut against the distal end of the impression pin and further comprises a central bore extending substantially therethrough. Advantageously, the cap screw may be selectively engaged or abutted to the impression pin for use in a closed-tray impression technique or the embedment cap may be selectively engaged or abutted to the impression pin for use in an open-tray impression technique.

In accordance with another embodiment the present invention provides a transfer impression coping. The trans-fer impression coping includes an impression pin having a body portion having a proximal end and a distal end. The proximal end is configured and adapted to be secured to the implant. The proximal end further comprises an indexing boss or recess formed therein for interlockingly engaging a corresponding mating indexing boss or recess formed on the implant. The impression pin has a central bore extending substantially completely through the impression pin and opening through the proximal and distal ends. A cap screw is further provided having a cap portion and a threaded shaft portion. The threaded shaft portion is adapted to pass through the bore extending through the impression pin and to threadingly engage a threaded bore of the implant. The cap portion is further adapted to selectively matingly engage or abut against the distal end of the impression pin.

In accordance with another embodiment the present invention provides a pick-up impression coping for use in taking an accurate dental impression of an implant installed in patient's jawbone. The pick-up impression coping includes an impression pin, including a body portion having a proximal end and a distal end. The proximal end is configured and adapted to be secured to the implant. The proximal end further comprises an indexing boss or recess formed therein for interlockingly engaging a corresponding mating indexing boss or recess formed on the implant. The impression pin has a central bore extending substantially completely through the impression pin and opening through the proximal and distal ends. An embedment cap is provided having one or more impression gripping elements and being adapted to selectively matingly engage or abut against the distal end of the impression pin. The embedment cap has a central bore extending substantially therethrough. A bolt or screw is provided having a head portion and a threaded shaft portion. The bolt or screw is sized and adapted to pass through the bore extending through the embedment cap and through the bore extending through the impression pin and to threadingly engage the threaded bore of the implant.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and its essential features and advantages, certain preferred embodiments and modifications thereof will become apparent to those skilled in the art from the detailed description herein having reference to the following figures, of which:

FIGS. 7A–H are detailed mechanical illustrations showing particular preferred geometries and preferred nominal dimensions of one particularly preferred embodiment of a universal impression pin having features and advantages in accordance with the present invention;

FIG. 16A is a schematic illustration of a multi-orientation impression coping in which the axis passing through the body of the impression coping is not parallel to the axis passing through the recessed area;

FIG. 16B is a schematic illustration of a multi-orientation impression coping of FIG. 16A situated over a dental implant fixture;

DETAILED DESCRIPTION OF THE PREFERRED EMBODIMENTS

Figure 1A:
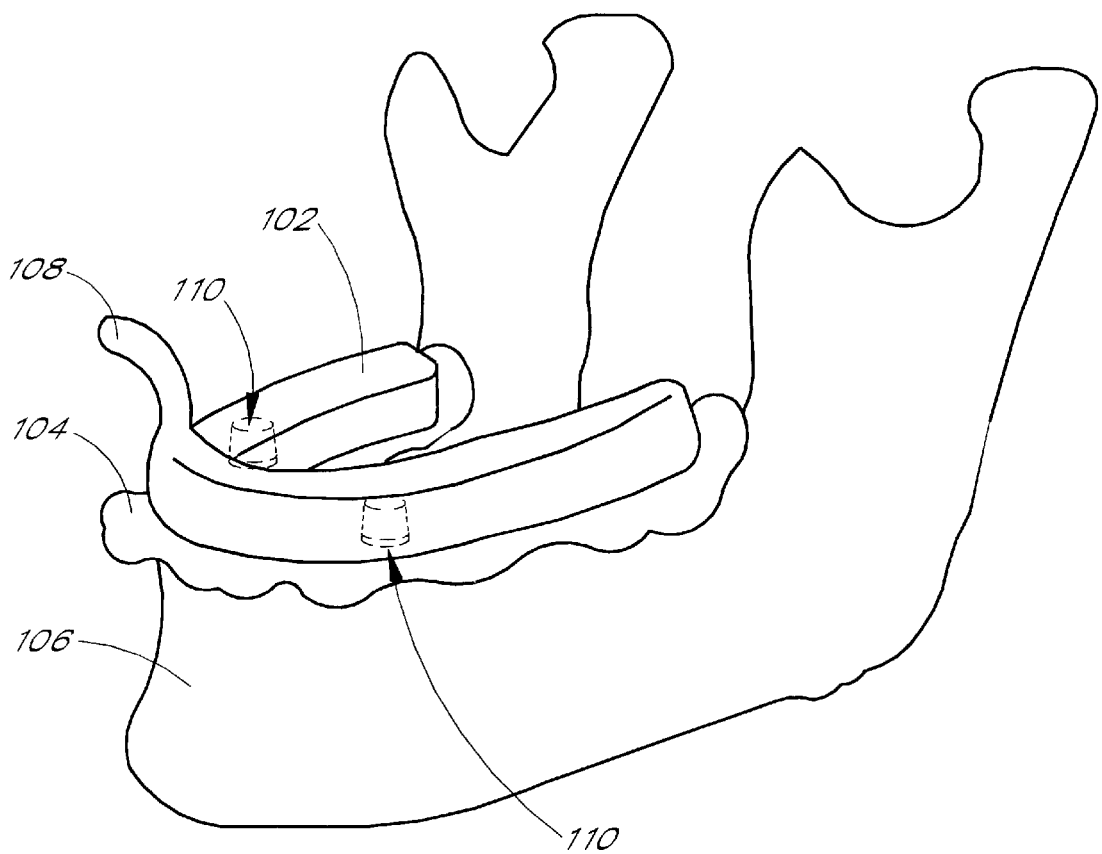
FIGS. 1A and 1B are schematic side perspective views of a closed impression tray with impression material applied to a patient's jawbone.

Two alternative impression techniques are known and used by restorative dentists to take an impression of a patient's mouth in order to prepare a tooth restoration. These are the closed-tray technique and the open-tray technique. In the closed-tray technique, as illustrated in FIGS. 1A,B, a generally U-shaped impression tray 102 is filled with an impression material 104 and is placed in the patient's mouth over the implant site, in this case the mandibular jawbone 106. The patient bites down on the tray, squeezing the impression material into the implant site and around the transfer impression copings 110 and any adjacent teeth (not shown). Within a few minutes, the impression material cures or hardens to a flexible, resilient consistency.

Figure 1B:
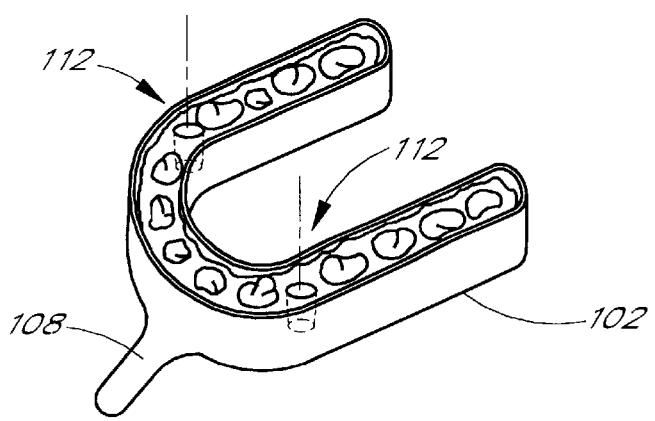

The impression tray 102 is then removed from the patient's mouth (FIG. 1B) to reveal an impression of the implant site and the impression copings 110. A handle 108 is typically provided on the impression tray 102 to facilitate such placement and removal of the tray 102 in the patient's mouth. The location and orientation of the impression copings 110 is thus recorded in the impression material in the form of indentations or impressions 112. In accordance with well-known techniques, the restorative dentist then removes the transfer impression copings 110 from the patient's mouth and reinserts them into the impression material in the formed indentations 112, being careful to preserve their proper orientation.

Figure 2A:
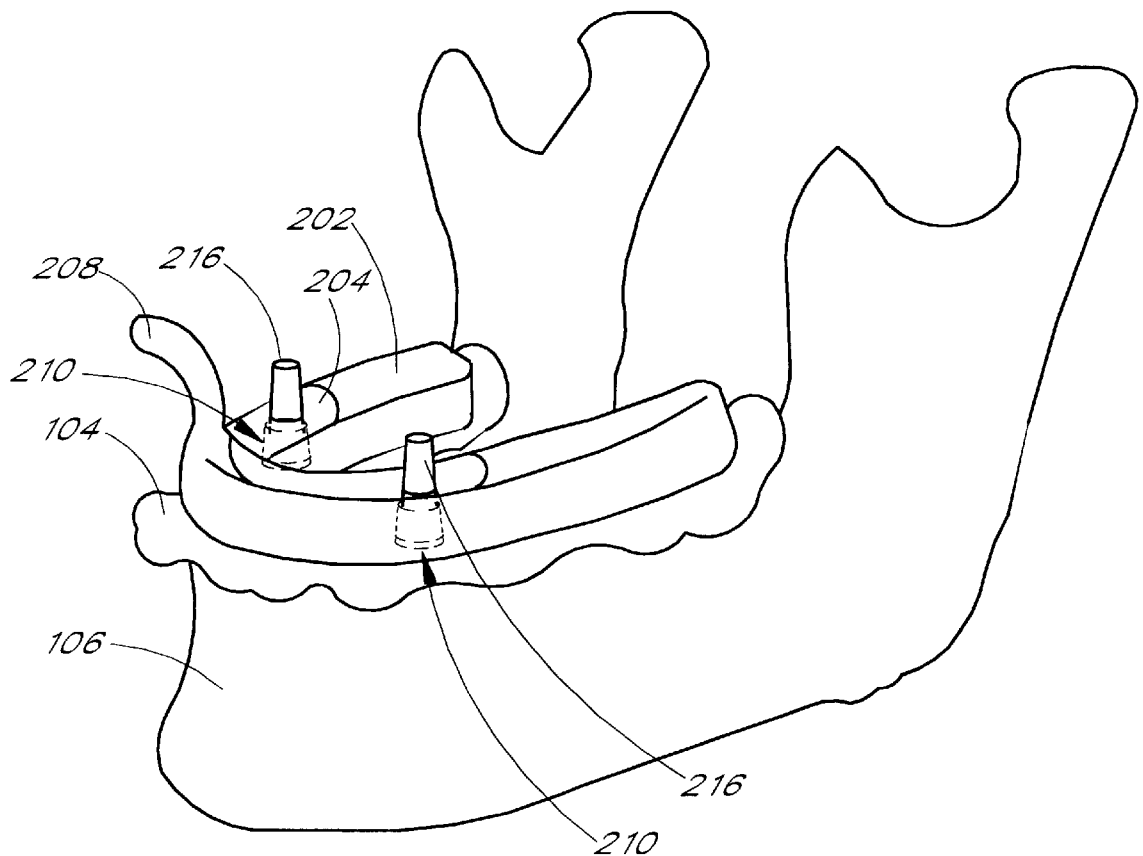
FIGS. 2A and 2B are schematic side perspective views of an open impression tray and impression material applied to a patient's jawbone.

FIGS. 2A,B show application of the conventional open-tray impression technique. In this case, an impression tray 202 is provided having an opening 204 therein. The impression tray 202 is filled with an impression material 104 and is placed in the patient's mouth over the implant site, again the mandibular jawbone 106. The patient bites down on the tray, squeezing the impression material into the implant site and around the pick-up impression copings 210 and any adjacent teeth (not shown). Retaining screws or bolts 216 securing each impression coping 210 extend through the opening 204 provided in the impression tray 202. Within a few minutes, the impression material 104 cures or hardens to a flexible, resilient consistency.

Figure 2B:
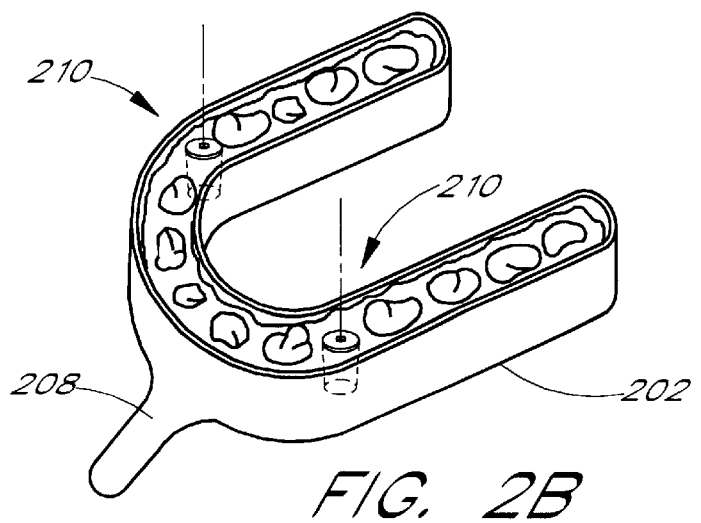

A tool is then used to loosen the screws or bolts 216 securing each impression coping 210 and the entire assembly, including the impression tray 202 and the copings 210, are removed from the patient's mouth (FIG. 2B). Thus, the impression copings 210 are removed with the impression material 104 from the patient's mouth. Such open tray technique is particularly useful for multi-site dental restorations, especially when the divergence angle between adjacent implants is, for example, greater than 30°. Such large divergence angle would make the closed-tray technique difficult if not impossible due to inherent difficulties in separating the impression tray and impression material from an implant site including adjacent divergent impression copings.

As noted above, the choice of whether to use the open- or closed-tray technique will be based on the particular patient's needs and the preference of the clinician. Often, however, the restorative dentist or clinician will not make a final decision on which technique to use until after final examination of the patient and the implant site(s). At that time a judgement call will be made and the clinician will choose one technique or the other depending upon prevailing patient indications. But because each technique, as conventionally practiced, requires a different impression coping, restorative dentists are required to maintain inventories of both transfer (closed-tray) impression copings and pick-up (open-tray) impression copings, including various sizes and types as may be required for use with a range of patients and procedures. This increases the overhead costs and administrative burdens of the restorative dentist, ultimately resulting in more expensive restorative dental procedures.

Figure 3:
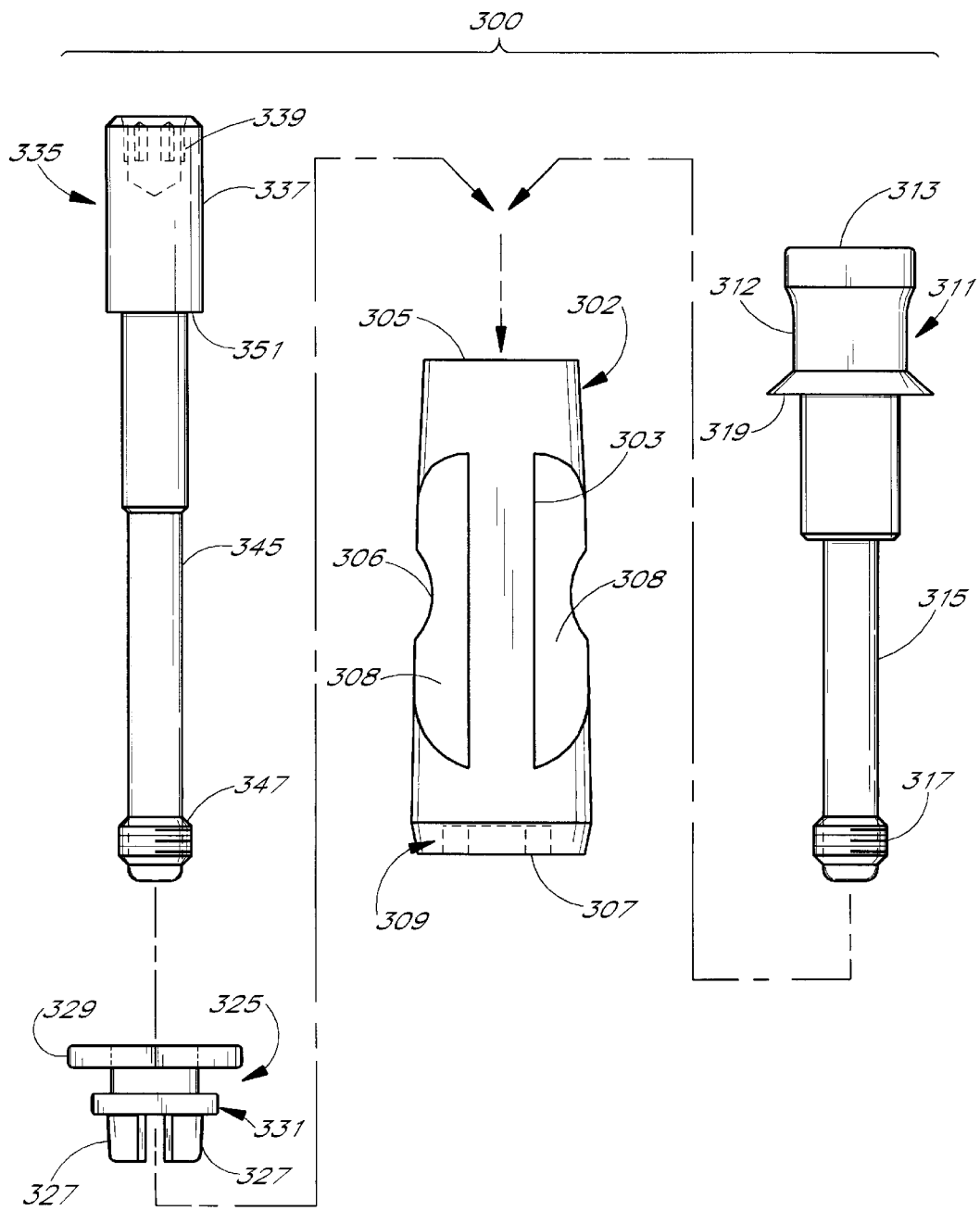
FIG. 3 is an exploded assembly view of a universal impression coping system having features and advantages in accordance with the present invention.

The present invention, in accordance with one embodiment, reduces these costs and administrative burdens by providing a universal impression coping system which is adapted to be used efficaciously in both open-tray and closed-tray dental impression techniques. FIG. 3 illustrate one preferred embodiment of a universal impression coping system 300 having features and advantages in accordance with the present invention. The system generally comprises a central body portion or impression pin 302 having a top portion 305 and a bottom portion 307. Preferably, the impression pin is between about 0.25 and 0.5 inches in length and between about 0.10 and 0.20 inches in diameter. Most preferably, the impression pin is about 0.43 inches in length and about 0.16 inches in diameter.

A through-hole (not shown) traverses longitudinally through the impression pin 302 from top 305 to bottom 307. The bottom 307 is further provided with an indexing means in the form of a recessed female hex 309 for mating with a conventional male hex indexing means of an implant fixture (not shown). The particular size and shape of the indexing means 309 is not important for purposes of practicing the present invention and a wide variety of other suitable shapes may alternatively be used with efficacy, giving due consideration to the goals of providing repeatable indexing and anti-rotation of mating components.

A pair of longitudinally-extending key-ways 308 are formed in the impression pin 302 along substantially most of the length thereof to provide registration means for assisting in maintaining the proper orientation of the impression pin when it is reinserted into the impression material (closed tray technique). Similarly, a shallow annular band or waist 306 is provided in the middle portion at least part way around the impression pin to provide sensory-tactile feedback to the clinician to indicate when the impression pin is fully reinserted in the impression material (closed tray technique).

For closed-tray configuration (transfer impression coping) a cap screw 311 is provided having a cap portion 313 and a shaft portion 315 having threads 317 formed on a distal end thereof. In use, the cap screw 311 is passed through the central bore (not shown) of the impression pin 302 until the shoulder 319 of the cap portion 313 abuts against the top 305 of the impression pin 302. The threads 317 of shaft 315 may then extend into the central threaded opining of an implant fixture to temporarily secure the resulting impression coping assembly to the implant. Optionally, suitable driving means such as a female hex (not shown) may be provided in the cap portion 313 of the cap screw 311, if desired, to assist in the securement of the impression coping assembly. Alternatively, this feature may be omitted and the cap screw 311 may be hand tightened or tightened by other means as may be convenient or expedient. The shaft 315 of the cap screw 311 is preferably between about 0.25 and 0.75 inches in length and most preferably about 0.5 inches in length. The cap portion 313 of the cap screw 311 is preferably between about 0.10 and 0.20 inches in length and most preferably about 0.15 inches in length. The cap portion 313 further preferably has a necked-down portion 312 with a diameter reduced by about 10–20% and having a smooth radius at the top portion thereof.

For open-tray configuration (pick-up impression coping) an embedment cap 325 is provided. The embedment cap 325 preferably includes two or more flexible fingers 327 adapted to frictionally secure the embedment cap 325 to the top 305 of the impression pin 302 by frictionally engaging the inner surface of the central bore thereof (not shown). On top of the embedment cap 325 are formed a pair of generally square plates 329, 331 approximately 0.17 inches square and rotated axially 45 degrees relative to one another. These plates 329, 331 help the embedment cap 325 grip the impression material. The embedment cap further includes a central bore (not shown) formed therethrough for receiving a bolt 335.

The bolt 335 includes an extended head portion 337 having a length preferably between about 0.10 and 0.30 inches and most preferably about 0.20 inches. Preferably a driving means 339 is formed in the head portion 337 for receiving a mating driving tool (not shown) such as an allen wrench or screw driver. The bolt 335 further includes a shaft 345 approximately 0.5 inches in length and having a threaded portion 347 thereon for engaging the threaded central bore of an implant fixture (not shown). In use, the bolt 335 is passed through the central bores (not shown) of both the embedment cap 325 and the impression pin 302 until the shoulder 351 of the extended head portion 337 of the bolt 335 abuts against the top square plate 329 of the embedment cap 325. The threads 347 of shaft 345 may then extend into the central threaded opining of an implant fixture to temporarily secure the resulting impression coping assembly to the implant.

Figure 4A:
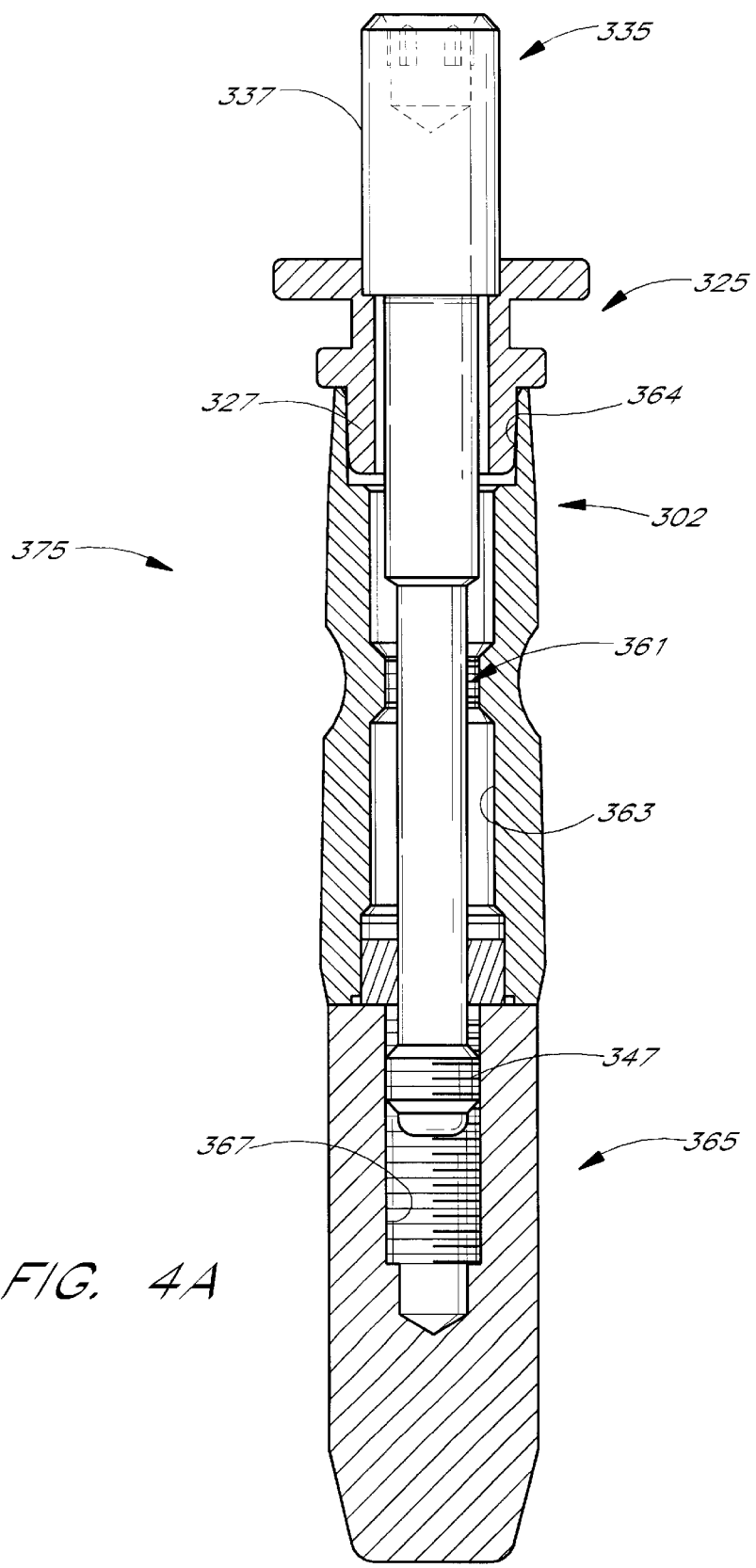
FIG. 4A is front elevation partial cut-away view of the universal impression coping system of FIG. 3 configured for use in an open-tray impression technique.
Figure 5:
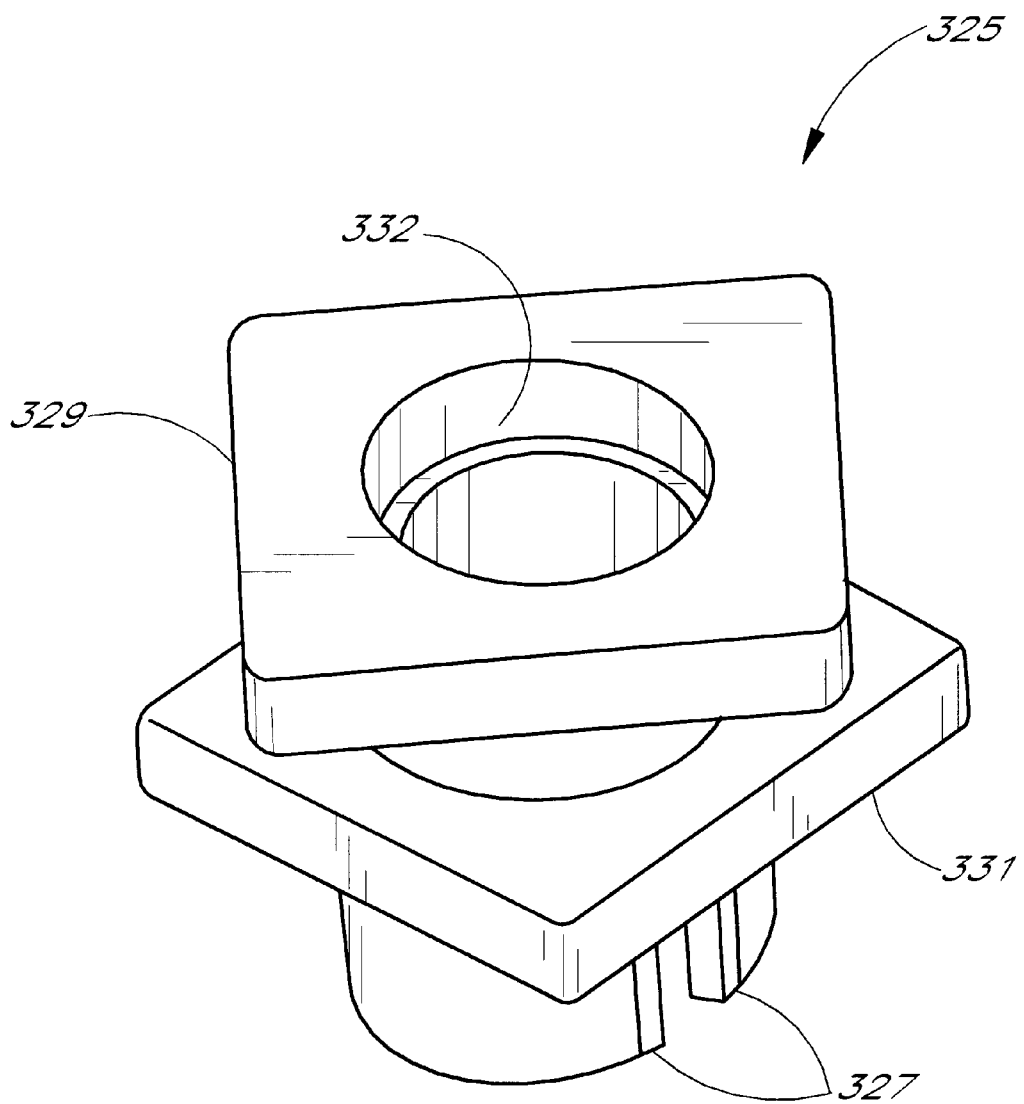
FIG. 5 is a perspective view of an embedment cap for use in accordance with the universal impression coping system of FIG. 4A.

FIG. 4A illustrates the universal impression pin system of FIG. 3 configured for use in an open-tray impression technique. In this case, a pick-up impression coping assembly 375 is formed comprising impression pin 302, embedment cap 325 and bolt 335. As noted above, the embedment cap 325 preferably includes two or more flexible fingers 327 adapted to frictionally secure the embedment cap 325 to the top 305 of the impression pin 302 by frictionally engaging the inner surface of a recessed bore 364 thereof. On top of the embedment cap 325 are formed a pair of generally square plates 329, 331 approximately 0.17 inches square and rotated axially 45 degrees relative to one another. These plates 329, 331 help the embedment cap 325 grip the impression material. The embedment cap further includes a central bore 332 formed therethrough for receiving the bolt 335. These features are illustrated more clearly in FIG. 5.

Internal capture threads 361 are preferably provided in the central bore 363 of the impression pin 302 for engaging threads 347 of the bolt 335. This provides for advantageously capturing the bolt 335 so that it cannot inadvertently be dislodged from the coping assembly 375. In use, the bolt 335 is used to temporarily secure the coping assembly 375 to an implant fixture 365 via the threaded central bore 367 thereof.

In the preferred embodiment illustrated, the pick-up impression coping assembly 375 uses a bolt 335 approximately 16 millimeters long, with an approximately 0.050-inch internal hex driving means. The dimensions of the screw, coping cap, and coping, and the shape and diameter of the hex, can vary widely and may be adjusted or modified based on factors well known to those skilled in the art. The length of the extended head portion 337 of the bolt 335 is preferably sufficient to allow the head 337 to protrude through the embedment cap 325 and through the top of the open tray 202 (FIG. 2A) so that the bolt 335 may be accessed and loosened prior to pulling the tray 102 from the patient's mouth and thereby allowing pick-up and/or capturing of the impression coping assembly 375 by the impression material.

Figure 4B:
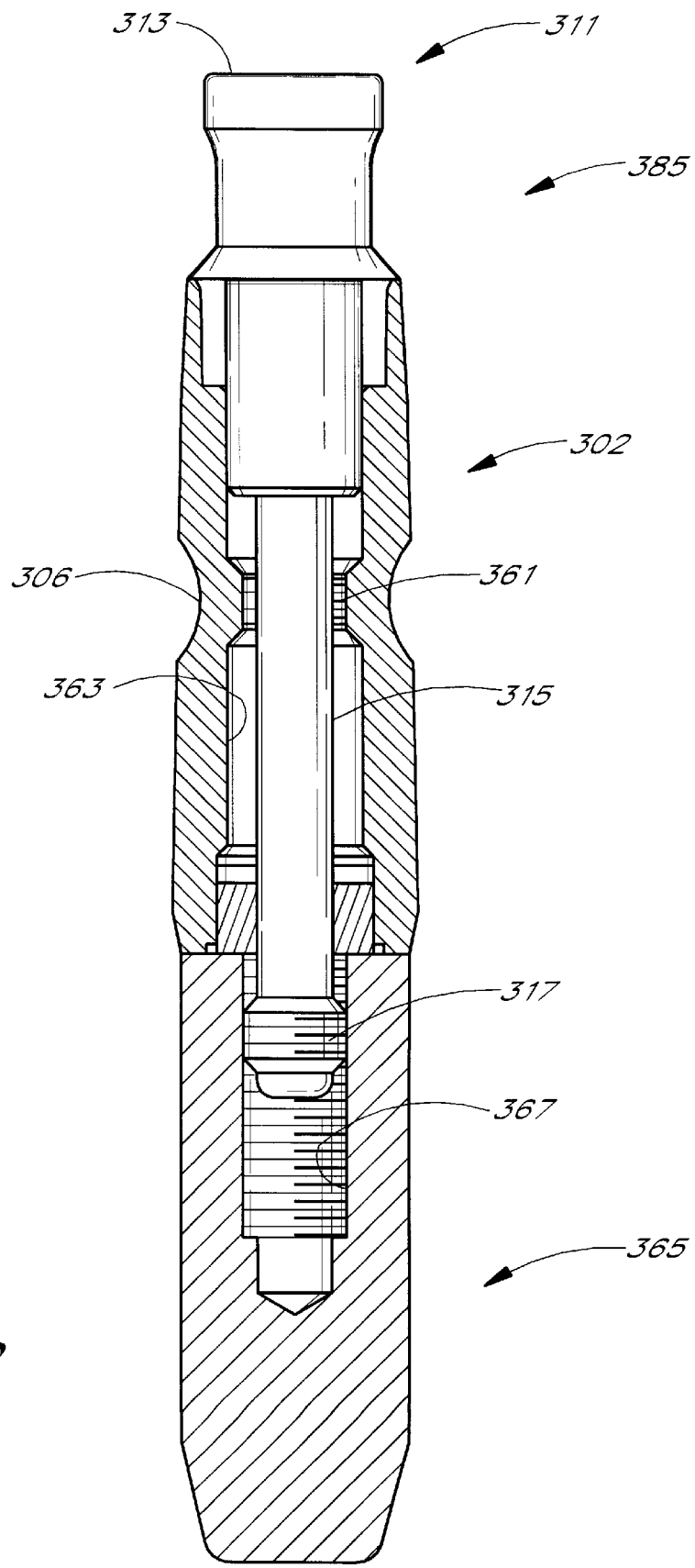
FIG. 4B is front elevation partial cut-away view of the universal impression coping system of FIG. 3 configured for use in an closed-tray impression technique.

FIG. 4B illustrates the universal impression pin system of FIG. 3 configured for use in a closed-tray impression technique. In this case, a transfer impression coping assembly 385 is formed comprising the impression pin 302 and the cap screw 311. Again internal capture threads 361 are preferably provided in the central bore 363 of the impression pin 302 for engaging threads 317 of the cap screw shaft 315. Again, this provides for the advantageous situation whereby the cap screw 311 is captured by the impression pin 302 so that it cannot inadvertently be dislodged from the coping assembly 385. In use, the cap screw 311 is passed through the impression pin 302 and is used to temporarily secure the coping assembly 385 to an implant fixture 365 via the threaded central bore 367 thereof.

In the preferred embodiment illustrated, the transfer impression coping assembly 385 uses a cap screw 311 having a shaft approximately 0.50 inches long and having a cap portion approximately 0.15 inches tall and 0.13 inches in diameter at the widest part. Again, the particular dimensions of the cap screw 311 and impression pin 302 can be varied widely and will be determined based on factors known to those skilled in the art. Preferably a shallow band or waist 306 is provided at least partially around the middle of the impression pin 302 to provide tactile-sensory feedback to the clinician to help ensure proper reinsertion of the coping assembly 385 into the impression material upon taking of the closed tray impression.

Figure 6:
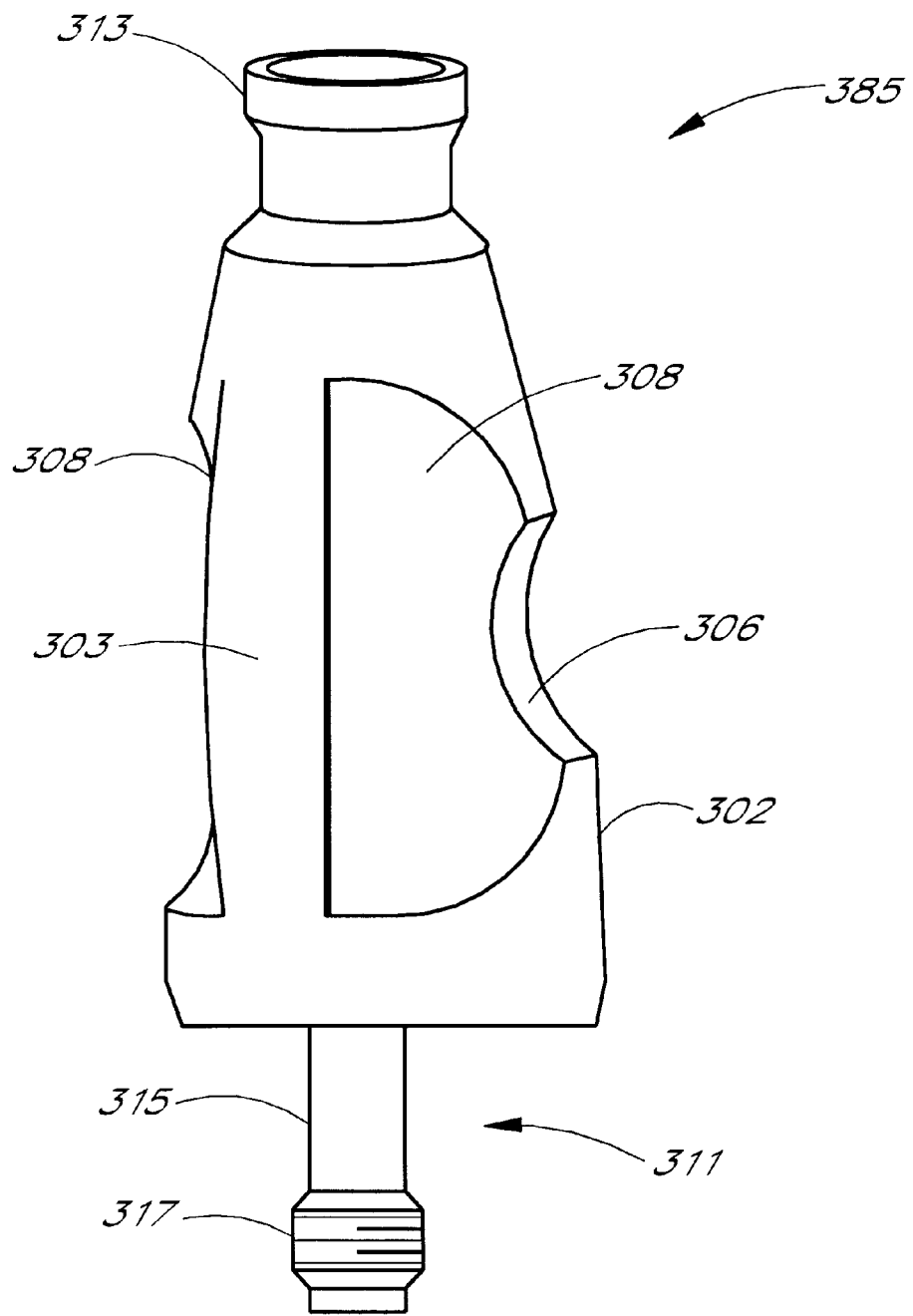
FIG. 6 is a front perspective view of the universal impression coping system of FIG. 3 configured for use in an closed-tray impression technique.

FIG. 6 is a front perspective illustration of the transfer impression coping assembly 385 of FIG. 4B, illustrating in more detail the preferred registration and sensory-tactile features thereof. As shown in FIG. 6, the transfer coping assembly 385 includes a lower body portion comprising the universal impression pin 302 and an upper cap portion 313 comprising the head of cap screw 311. The cap screw 311 has a shaft 315 extending through the coping assembly 385 and a threaded portion 317 at a depending end thereof for engaging the threaded central bore of an implant fixture (not shown).

A pair of longitudinally-extending key-ways 308 are formed in the impression pin 302 along substantially most of the length thereof defining therebetween a longitudinally extended projecting portion 303. Advantageously, key ways 308 and projecting portion 303 provide a unique (one orientation only) registration of the coping assembly 385 in the impression material, thereby ensuring precise and proper orientation of the impression coping assembly 385 when it is reinserted into the impression material following taking of a closed tray impression. The particular illustrated size, shape and configuration of the key ways 308 and projecting portion 303 provide increased visual and tactile cues for the clinician to determine the one correct orientation of the coping within an impression left in an impression material. Thus, precision and accuracy of the impression is assured even if the coping itself is not perfectly symmetric and even if the key ways 308 are not precisely located and oriented on the impression pin 302.

A shallow annular band or waist 306 is provided along the middle portion of the impression pin 302 and extends roughly 180 degrees about the circumference of the impression pin 302, as illustrated. Waist 306 provides sensory-tactile feedback to a clinician to indicate when the impression coping assembly 385 is fully reinserted in the impression material during the transfer step of the closed tray impression technique. Preferably, the waist 306 does not extend through the projecting portion 303 so that adequate interference and tactile-sensory feedback is maintained in the event that the impression coping assembly 385 is inadvertently inserted into the impression material with an incorrect orientation relative to the residual coping impression.

Figure 8:
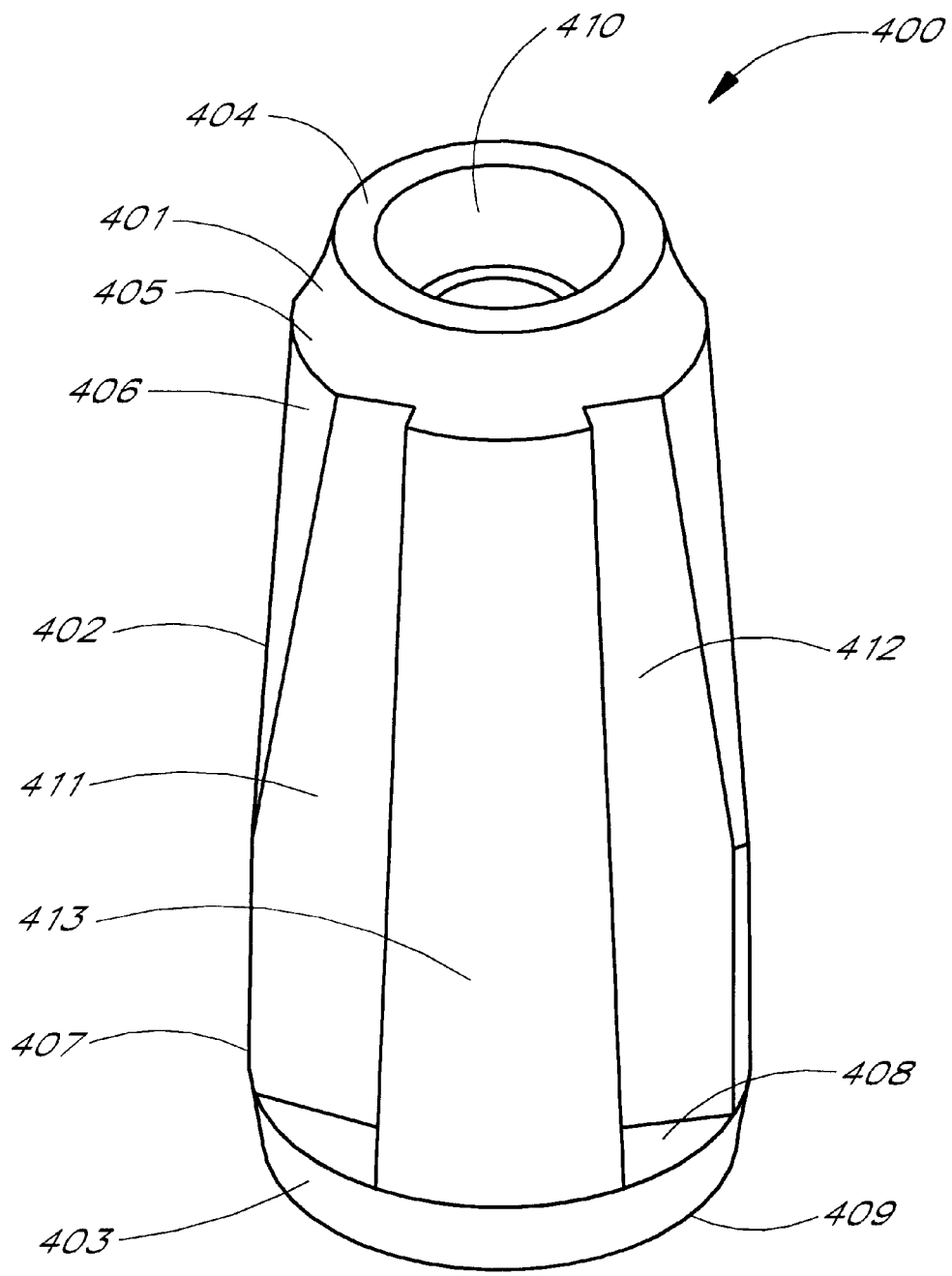
FIG. 8 is a front perspective view of an alternative embodiment of a universal impression pin having features and advantages in accordance with the present invention.
Figure 9:
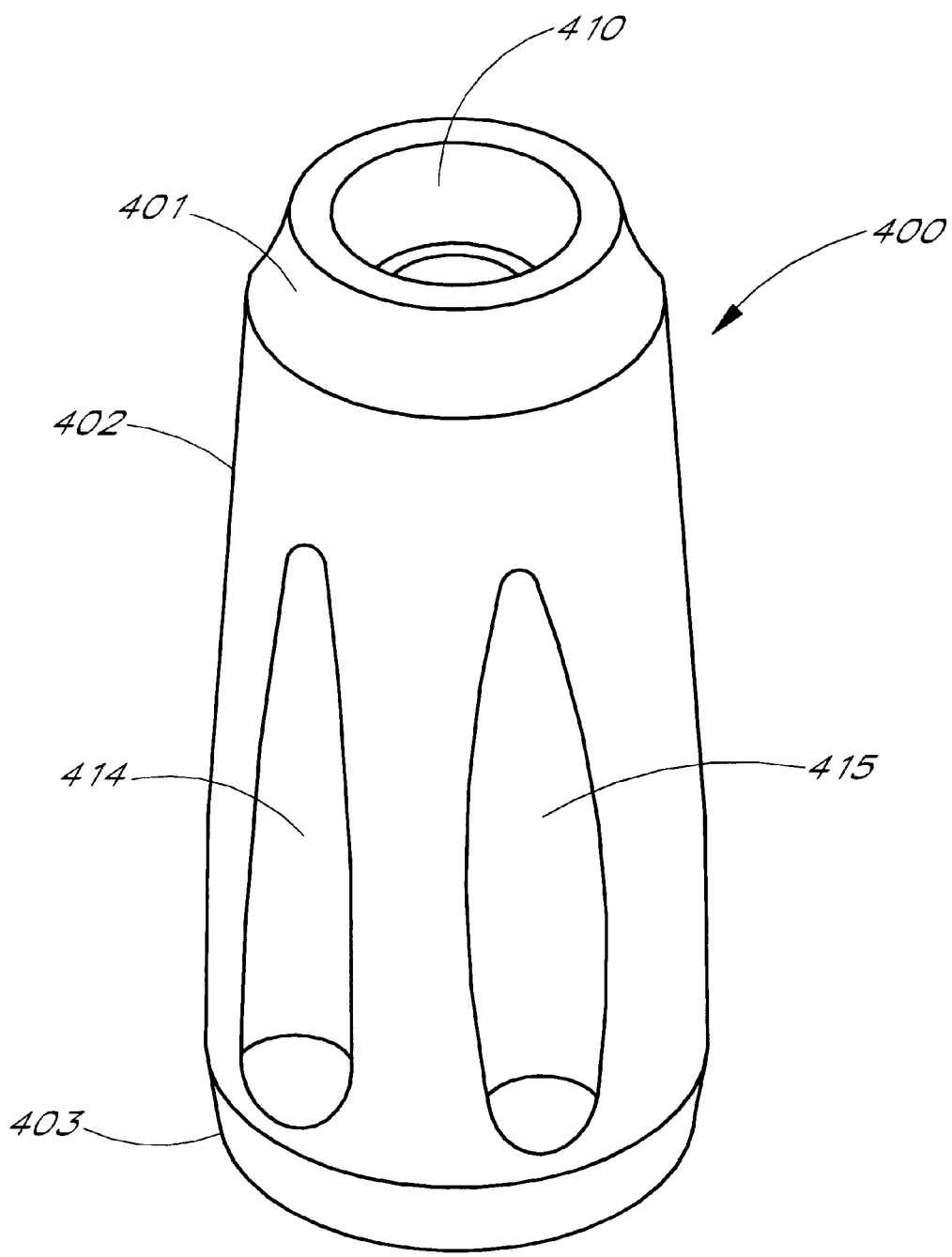
FIG. 9 is a rear perspective view of the universal impression pin of FIG. 8.

FIGS. 7A–H are detailed mechanical illustrations drawn roughly to scale and showing particular preferred geometries and indicating preferred nominal dimensions of one particularly preferred embodiment of a universal impression pin having features and advantages in accordance with the present invention. Referring to FIG. 7A, the diameter $D_A$ is about 3.35 mm (0.132 inches) and the angle $\theta_A$ is about 15°. Referring to FIG. 7B, the length $L_B$ is about 11.0 mm (0.434 inches), the diameters $D_{B1}$ and $D_{B2}$ are about 4.11 mm (0.162 inches), the diameter $D_{B3}$ is about 4.50 mm (0.177 inches) and the angle $\theta_B$ is about 5°. Referring to FIG. 7C, the length $L_{C1}$ is about 5.72 mm (0.225 inches), the length $L_{C2}$ is about 3.81 mm (0.150 inches), the length $L_{C3}$ is about 0.762 mm (0.030 inches), the width $W_C$ is about 1.65 mm (0.065 inches) and the radius of curvature $R_C$ is about 1.57 mm (0.062 inches). Referring to FIG. 7D, the length $L_{D1}$ is about 4.37 mm (0.172 inches), the length $L_{D2}$ is about 6.91 mm (0.272 inches) and the radii of curvature $R_{D1}$, $R_{D2}$ are typically about 3.18 mm (0.125 inches). Referring to FIG. 7E, the length $L_E$ is about 2.03 mm (0.080 inches). Referring to FIG. 7G, the length $L_{G1}$ is about 2.84 mm (0.112 inches), the $L_{G2}$ is about 3.38 mm (0.133 inches) and the radii of curvature $R_G$ are about 1.42 mm (0.056 inches). Referring to FIG. 7H, the length $L_H$ is about 0.965 mm (0.038 inches), the angles $\theta_{H1}$ are about 30° and the angles $\theta_{H2}$ are about 90°;

FIGS. 8 and 9 are front and rear perspective views, respectively, of an alternative embodiment of a universal impression pin 400 having features and advantages of the present innovation. The impression pin 400 generally comprises an upper portion 401, a middle portion 402, and a lower portion 403. The proximal end 405 of the upper portion 401 is joined to the distal end 406 of the middle portion 402. The proximal end 407 of the middle portion 402 is joined to the distal end 408 of lower portion 403. A bore 410 passes completely through the interior of impression pin 400 along its longitudinal axis.

Figure 10:
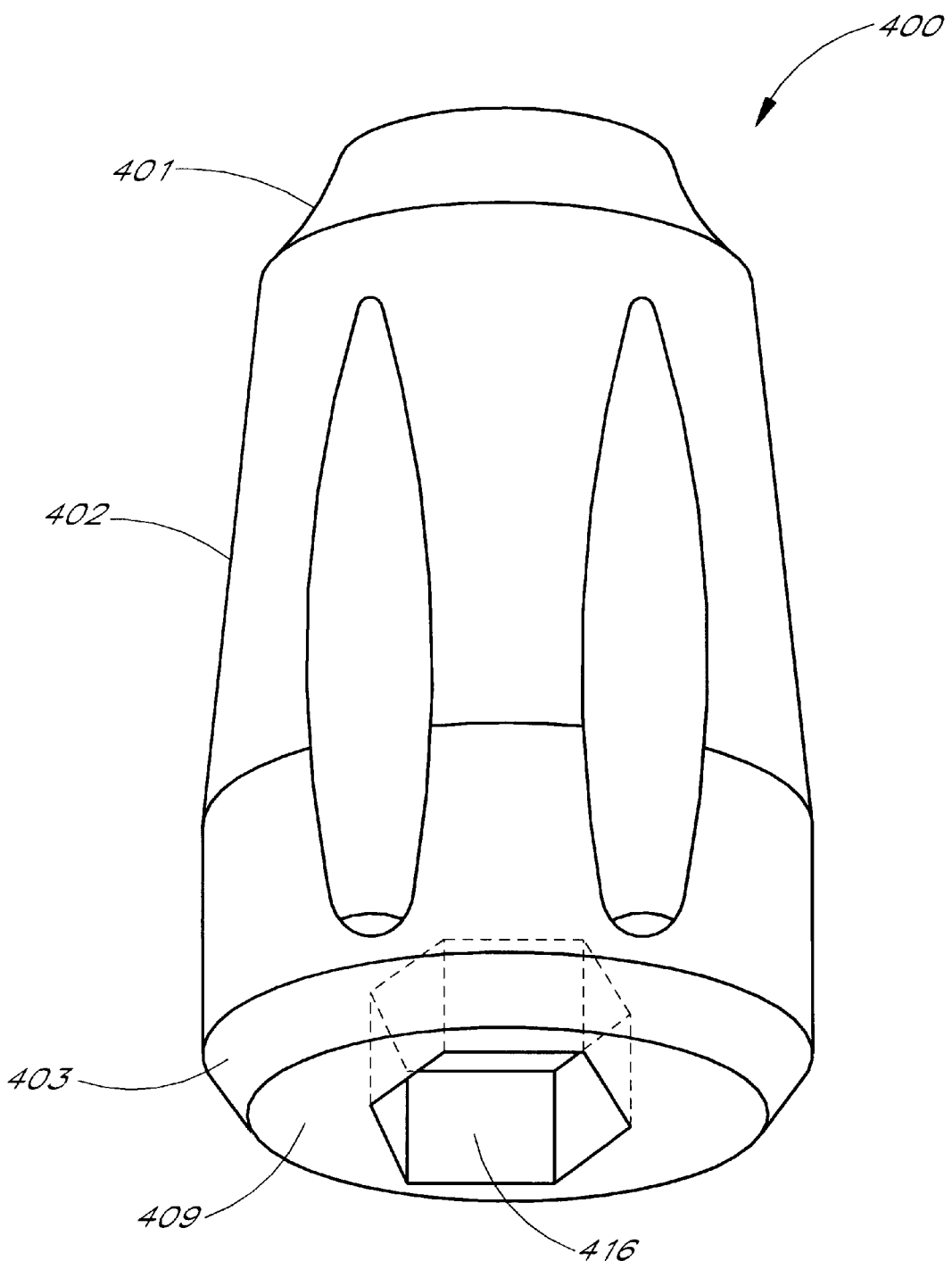
FIG. 10 is a bottom perspective view of the universal impression pin of FIG. 8.
Figure 11A:
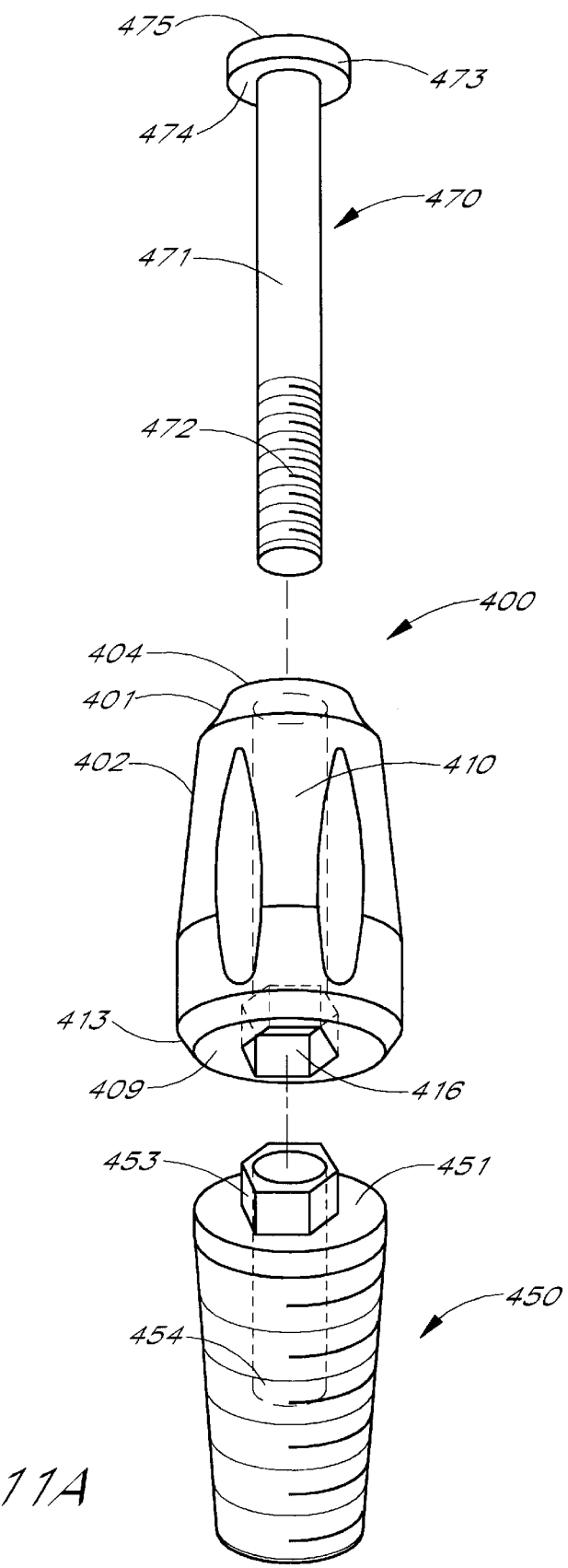
FIG. 11A is a perspective exploded assembly view of an alternative embodiment of a universal impression coping system having features and advantages in accordance with the present invention.

As shown in FIGS. 10 and 11A, the proximal end 409 of the lower portion 403 contains a recessed hexagonal area 416 having a geometric shape that corresponds to the raised hexagonal portion 453 on the distal end 451 of a dental implant fixture 450. Although the recessed area shown in FIGS. 10 and 11A is hexagonally shaped in order to correspond to the raised hexagonal portion 453 on the distal end 451 of the implant fixture 450, it would be understood by one of ordinary skill in the art that a variety of other geometric shapes (pentagon, square, asymmetrical shapes, etc.) could also be used for the recessed area in the impression coping, depending on the shape of the raised portion of the dental implant fixture. It is also understood that the depth of the recessed area 416 may extend through the lower portion 403 of the impression coping 400 and into the middle portion 402, if necessary to accommodate the corresponding raised portion of the implant fixture.

Figure 11B:
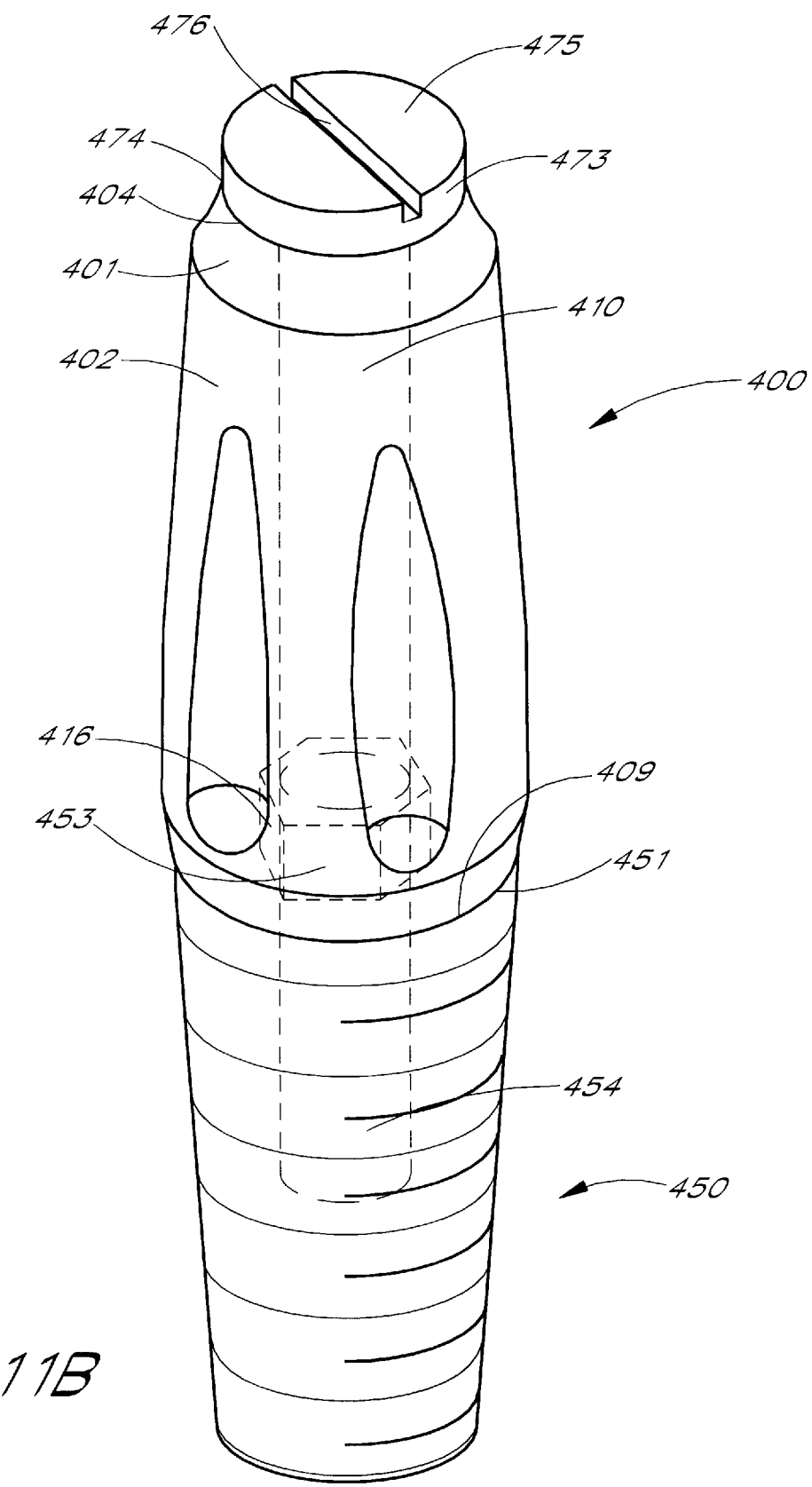
FIG. 11B is a perspective assembled view of the universal impression coping system OF FIG. 11A.

As shown in FIG. 11B, when the impression coping 400 is situated on top of a dental implant fixture 450, the raised hexagonal portion 453 on the distal end 451 of the implant fixture 450 mates with the recessed area 416 of the lower portion 403 of the impression coping 400. Regardless of any particular embodiment, it is desirable that the dimensions of the raised portion on the distal end of the implant fixture and the recessed area in the proximal end of the lower portion of the impression coping be substantially similar so as to prevent rotation of the impression coping with respect to the implant fixture along their common longitudinal axis, and to allow the proximal end of the lower portion of the impression coping to abut the distal end of the impression coping.

A central bore 454 passes through the raised hexagonal portion 453, and at least part way into the interior, of the dental implant fixture 450. A threaded screw 470, having a body 471, a threaded portion 472, and a head 473, passes though the bore 410 in the impression coping 400 and into the central bore 454 of the dental implant fixture 450. The threaded portion 472 of the screw 470 attaches to the appropriately sized, threaded interior 454 of the implant fixture 450. The proximal end 474 of the head 473 abuts the distal end 404 of the upper portion 401 of the impression coping 400, thereby preventing the impression coping 400 from detaching from the implant fixture 450. A slit 476 in the distal end 475 of the head 473 receives a device (not shown) for attaching the screw 470 to the dental implant fixture 450.

Referring again to FIGS. 8 and 9, the middle portion 402 of the impression coping 400 has a generally frustoconical shape, which tapers from its wider proximal end 407 to its narrower distal end 406. The angle of the taper through the middle portion 402 may change abruptly, forming one or more corners in the surface of the impression coping, or may change gradually and continuously, as desired or expedient. Furthermore, one or more sections of the middle portion 402 may be substantially vertical or tapered slightly outwardly.

Figure 12:
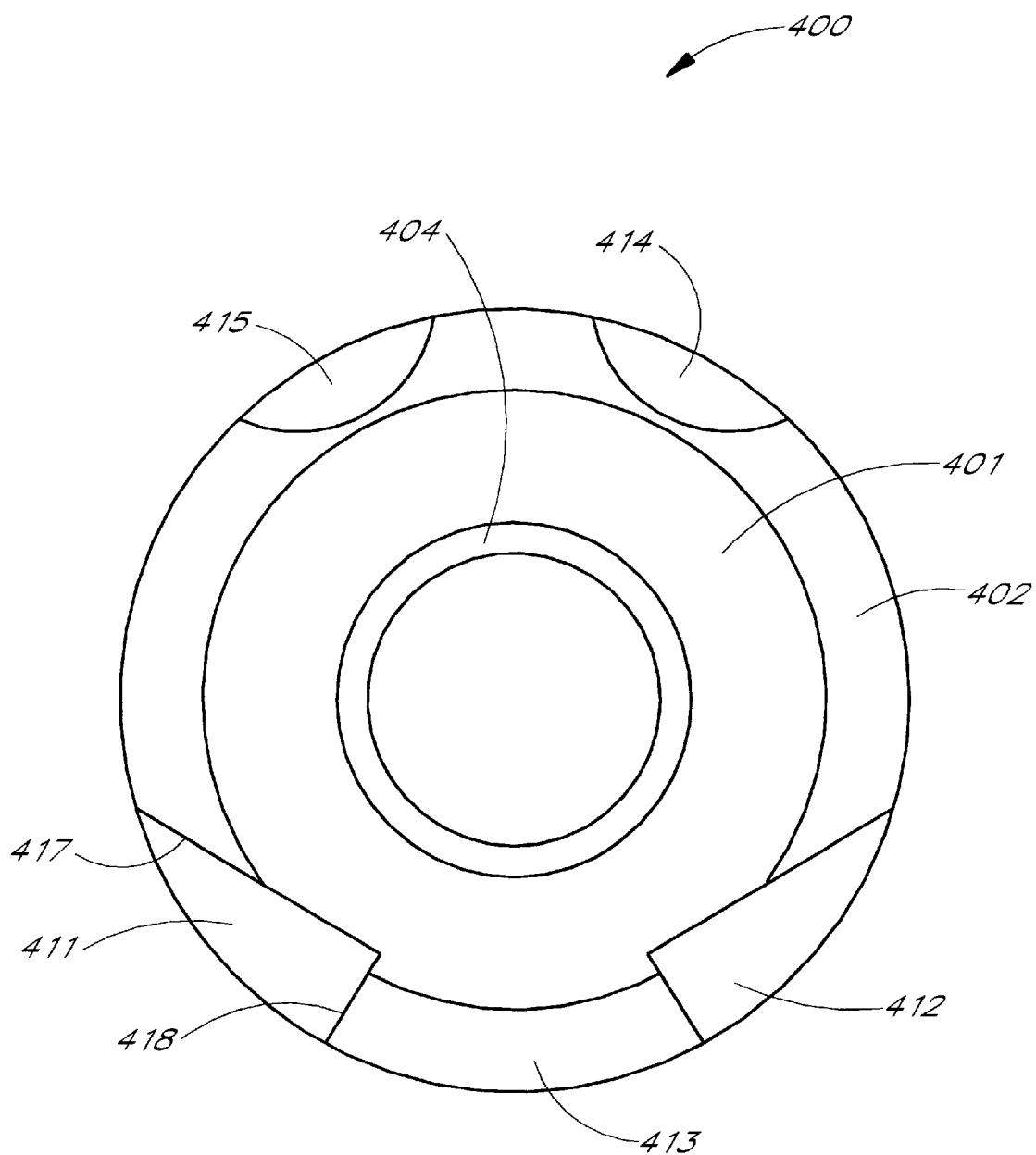
FIG. 12 is a top plan view of the impression coping of FIG. 8.

Various grooves are cut into the upper portion 401 and middle portion 402 of the impression coping 400 in a generally longitudinal direction. FIG. 12 is a top view of the impression coping illustrated in FIGS. 8 and 9 and illustrates this feature in more detail. Groove 411 is created by removing that section of the upper portion 401 and middle portion 402 defined by the two intersecting planes 417 and 418. In the preferred embodiment illustrated in FIGS. 8 and 12, plane 418 passes through the longitudinal axis of impression coping 400, and plane 417 is substantially perpendicular to plane 418 and also parallel to the longitudinal axis of impression coping 400. The angle formed by the intersection of the two planes preferably is between about 30 and 120 degrees, and most preferably is about 90 degrees. Groove 411 terminates at about the juncture of the middle portion 402 and the lower portion 403 of the impression coping 400. Groove 412 is substantially the mirror image of groove 411.

Grooves 411 and 412 define a section 413 of the middle portion 402. As shown more clearly in FIG. 12, the transverse cross-sectional shape of section 413 is approximately trapezoidal, except that the shape of the base of the trapezoid is determined by the general circumferential shape of the impression coping 400. Where the impression coping 400 is generally circular in shape, as shown in FIG. 12, for example, the base of the "trapezoid" is preferably slightly convex. Because of its general shape, section 413 is sometimes referred to herein as a "dove tail key."

Preferably, the horizontal width of the surface of section 413 is approximately one-third to one-twelfth the total circumference of the middle portion 402 of the impression coping 400. More preferably, the horizontal width of the surface of section 413 is approximately one-fourth to one-eighth the total circumference of the middle portion 402. Most preferably, the width of the surface of section 413 is about one-sixth the total circumference of the middle portion 402.

Each side of the section 413 dove tail key preferably is coplanar with a plane passing though the longitudinal axis of the impression coping 402. Optionally, as illustrated in FIG. 9, two circular grooves 414 and 415 may be cut into the rear of the middle portion 402 of the impression coping 400 in a generally longitudinal direction. The centers of the circles defining circular grooves 414 and 415 are each external to the circumference of the impression coping 400. One of ordinary skill in the art would understand, however, that either center may be within or collinear with the circumference of the impression coping 400, as desired. The midpoints of these circular grooves are approximately 60 degrees apart, although they may be closer or further apart as desired.

Figure 13:
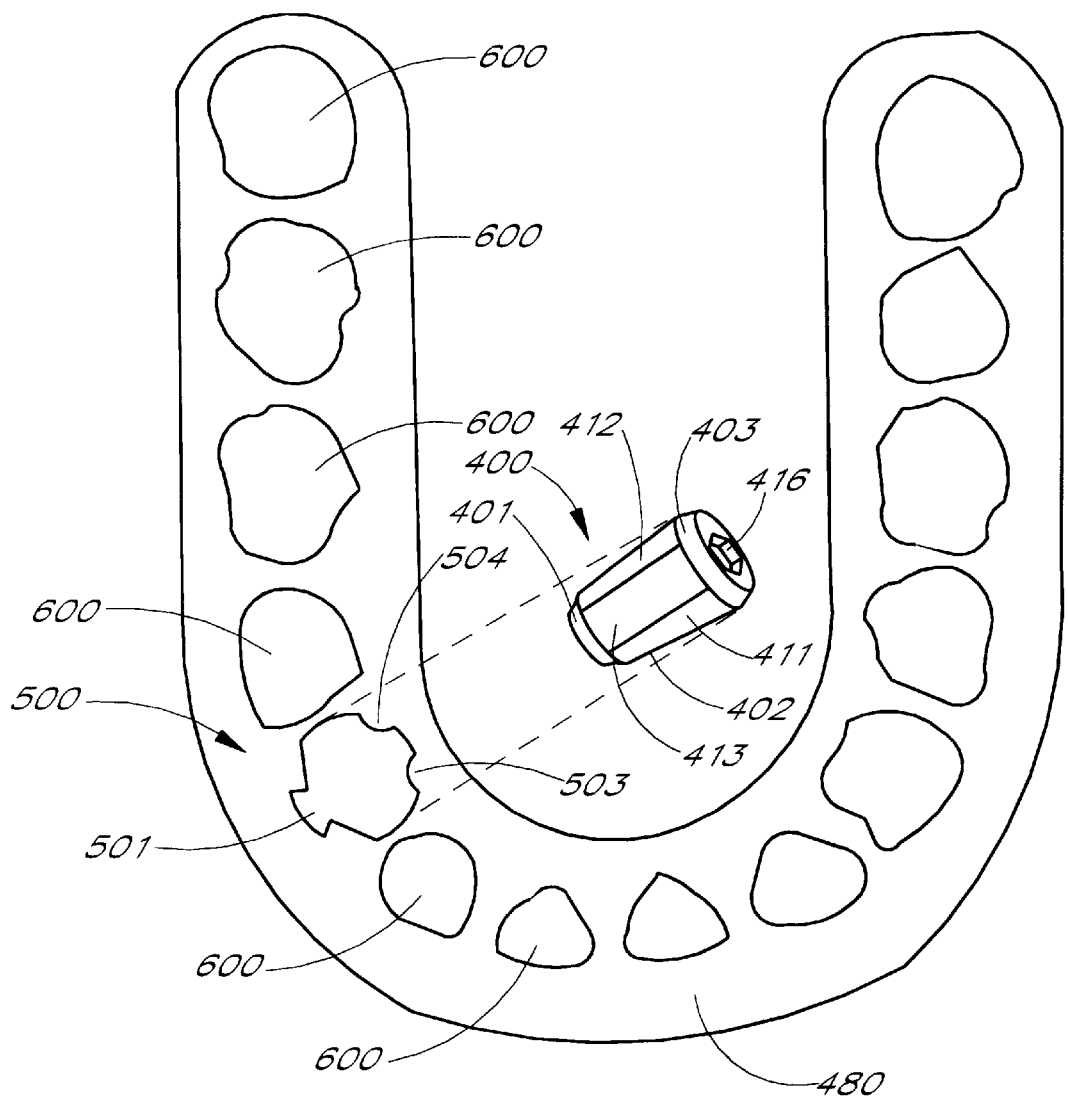
FIG. 13 is a partial schematic perspective view of an impression tray containing impression material, the impression left in impression material by the impression coping illustrated in FIG. 1, and the impression coping properly aligned for reinsertion into the impression material.

As illustrated in FIG. 13, when a transfer impression coping 400 having features of the invention is embedded within an impression material 480, an impression 500 is made. The impression material 480 also contains impressions 600 created by the patient's teeth surrounding the impression coping 400. A space 501 is made in the impression material by section 413 of the impression coping 400. Because of the general "dove tail key" shape of both section 413 and space 501, section 413 and space 501 form a dove tail joint when the impression coping 400 is reinserted into the impression material 480. No other part of the impression 500 is adapted to receive section 413 of impression coping 400 upon reinsertion into the impression material 480.

FIG. 13 also illustrates bulges 503 and 504 in the impression material 480, which are created by the optional circular grooves 414 and 415, respectively, of the impression coping 400. Upon reinsertion of the impression coping 400 into the impression 500, circular grooves 414 and 415 receive bulges 503 and 504, respectively, to form a secure fit. This particular arrangement of dove tail keys and circular grooves provides a secure fit between the impression coping 400 and the impression material 480.

Although the embodiment illustrated in FIGS. 8–13 comprises one dove tail key and two circular grooves, the present invention contemplates combining one or more dove tail keys with zero, one, or more circular grooves to create a suitable impression coping that resists undetected misalignment upon reinsertion into the impression material. Additionally, as shown in FIG. 13, the arrangement of one or more dove tail keys and circular grooves around the body of the impression coping allows the user to visually align the different sections and grooves in the impression coping with the corresponding spaces in the impression material before reinsertion. In FIG. 13, section 413 of the impression coping 400 is easily aligned with space 501 in the impression material 480 prior to reinsertion.

Figure 14:
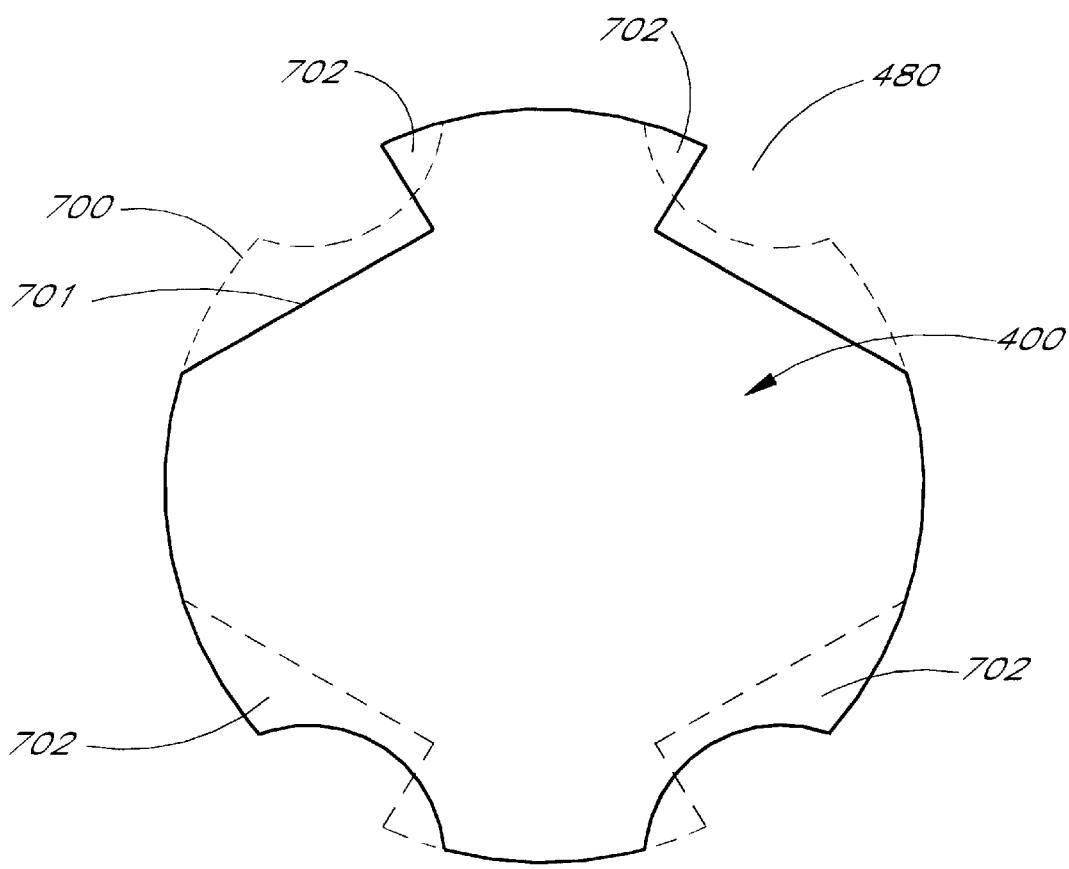
FIG. 14 is a schematic illustration of the interference between an impression pin having features of the present invention and an impression left in impression material by said impression pin.

FIG. 14 schematically illustrates a transverse cross-sectional view of the impression coping 400 and the impression material 480 when the impression coping 400 is misaligned before reinsertion into the impression material 480. The dotted line 700 defines the shape of the original impression left in the impression material 480 by the impression coping 400. The solid line 701 defines the shape of the impression coping 400 when misaligned before reinsertion. In FIG. 14, the impression coping 400 is misaligned by 180 degrees prior to reinsertion. Areas 702 show the extent of interference between the impression coping 400 and the space in the impression material 480 when the impression coping is reinserted improperly. This pattern of interference provides keen tactile sensation as the impression coping is reinserted into the impression material. This feature greatly reduces the risk of undetected misalignment of the impression coping 400.

In the preferred embodiment of the invention illustrated the impression coping 400 has only one possible orientation upon reinsertion into the impression material 480. A single-orientation impression coping overcomes several inherent disadvantages of multiple-orientation or so-called "self-indexing" impression copings. In the self-indexing copings any inaccuracies in the planes of symmetry will necessarily be transferred to the plaster analogue (and ultimately to the final restoration) whenever the impression coping is reinserted into the impression material in an "indexed" orientation other than the original indexed orientation.

Figure 15B:
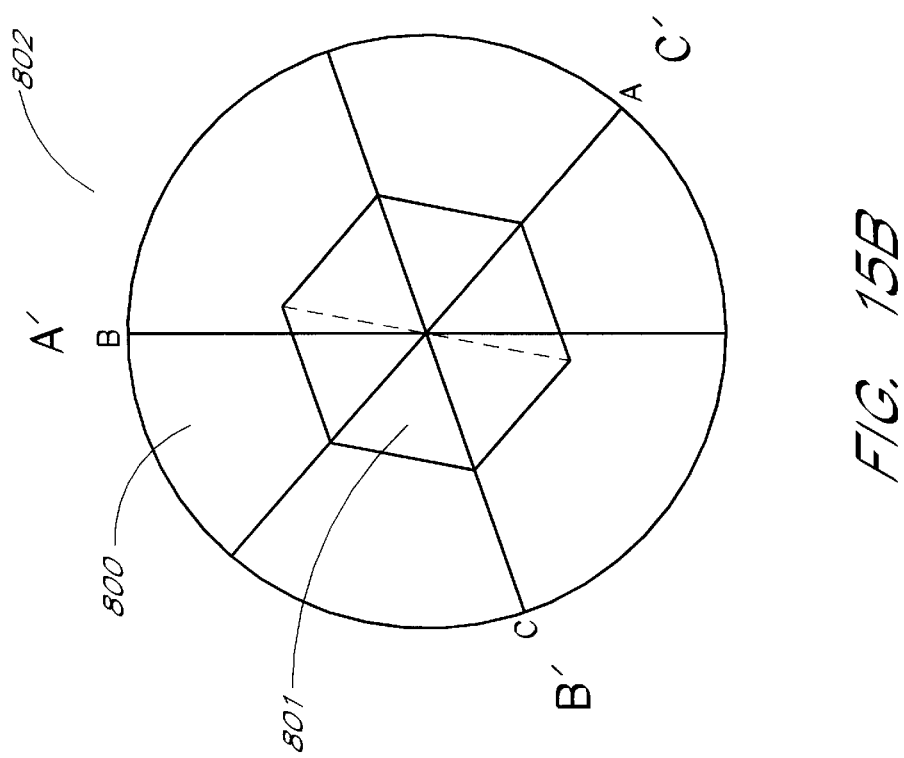
FIGS. 15A and 15B are top plan schematic views of a three-orientation impression coping in which the planes of symmetry of the body are not coplanar with the planes of symmetry of the recessed hexagonal area.
Figure 15A:
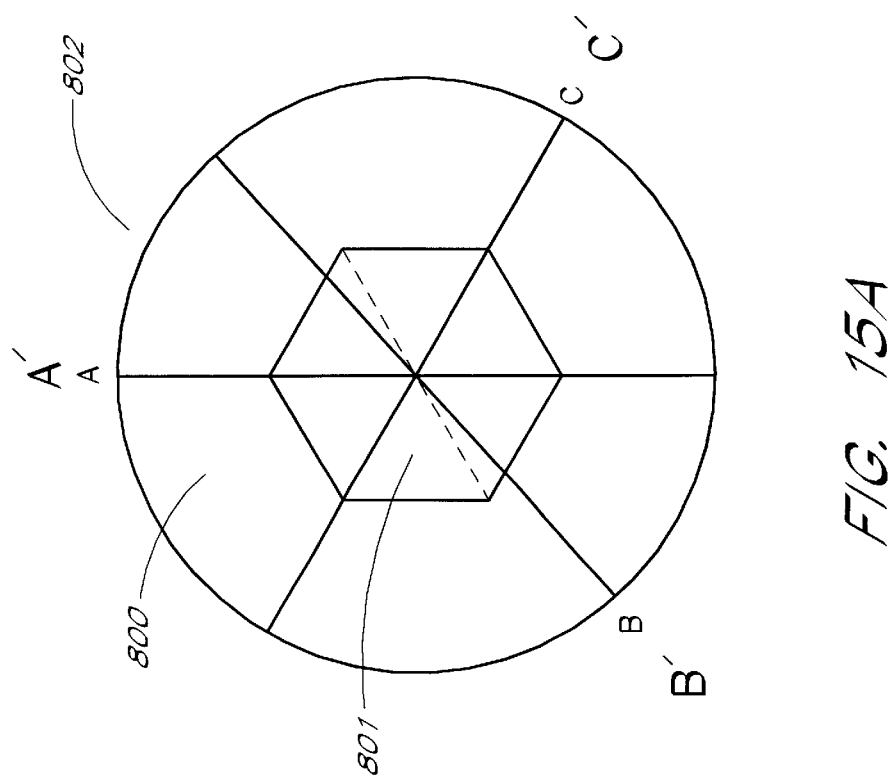

For instance, FIG. 15 illustrates the case where an impression coping 800 has a hexagonal recessed indexing means and wherein the coping is a self-indexing type capable of being inserted in three possible "indexed" orientations in the impression material. In this case, potential inaccuracies may occur in the symmetry of the registration means and/or the coping itself which may cause slight errors in the reinsertion and alignment of the impression coping 800 in the impression material. Assume, for example as shown in FIG. 15, that inherent inaccuracies exist to the extent that the planes of symmetry dividing the body of the impression coping are not evenly spaced. The body of the impression coping 800 has orientation points at A, B, and C that match point A', B', and C', respectively, in the impression material 802 (FIG. 15A). The planes of symmetry passing through points A and C are coplanar with two of the planes of symmetry dividing the hexagonal recessed area 801. The plane of symmetry passing through point B, however, is not coplanar with one of the planes of symmetry of the hexagonal recessed area 801. It can be seen that if the impression coping 800 of FIG. 15A is reinserted into the impression material 802 in its original orientation (i.e., point A aligned with point A' in the impression material 802), then the coping will be aligned. However, if the impression coping 800 is reinserted in an alternative indexed orientation where point B, for example, aligns with point A' in the impression material 802, then a corner of the hexagonal recessed area 801 will not be properly aligned with point A'. This inaccuracy ultimately will be transferred to the final restoration.

In order to overcome this inherent source of error while retaining the multiple-orientation self-indexing feature, extremely strict tolerances must be maintained when constructing the impression coping 800. Consequently, multiple-orientation impression copings of this design are more expensive to manufacture and are more prone to inaccuracies than single-orientation transfer impression copings, as in the present invention.

Figure 16C:
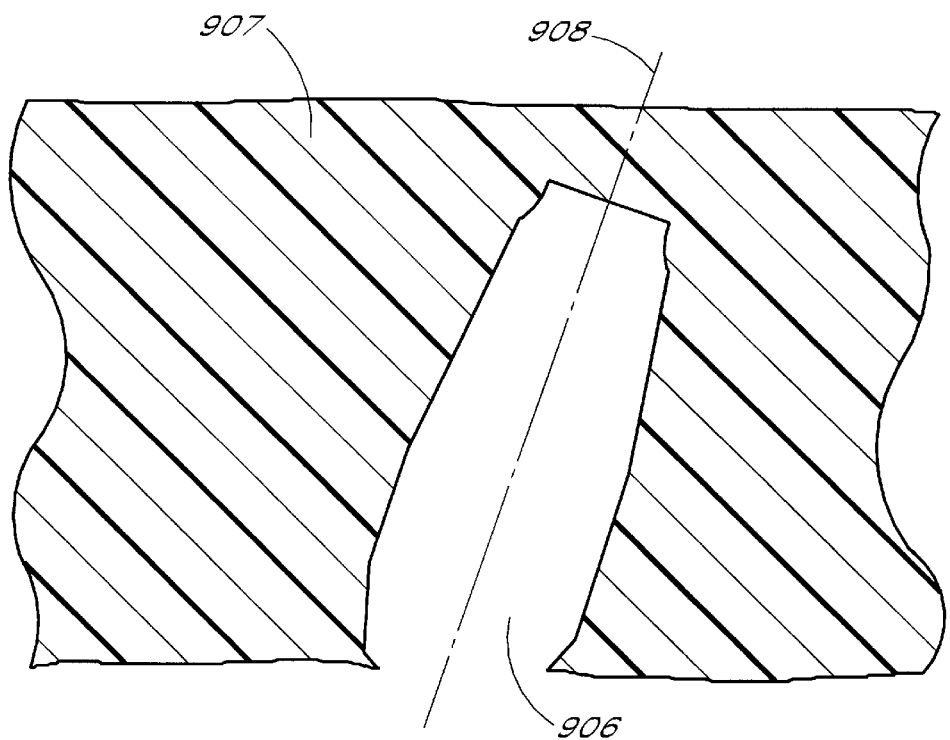
FIG. 16C is a schematic illustration of the impression left by the multi-orientation impression coping of FIG. 16B.
Figure 16D:
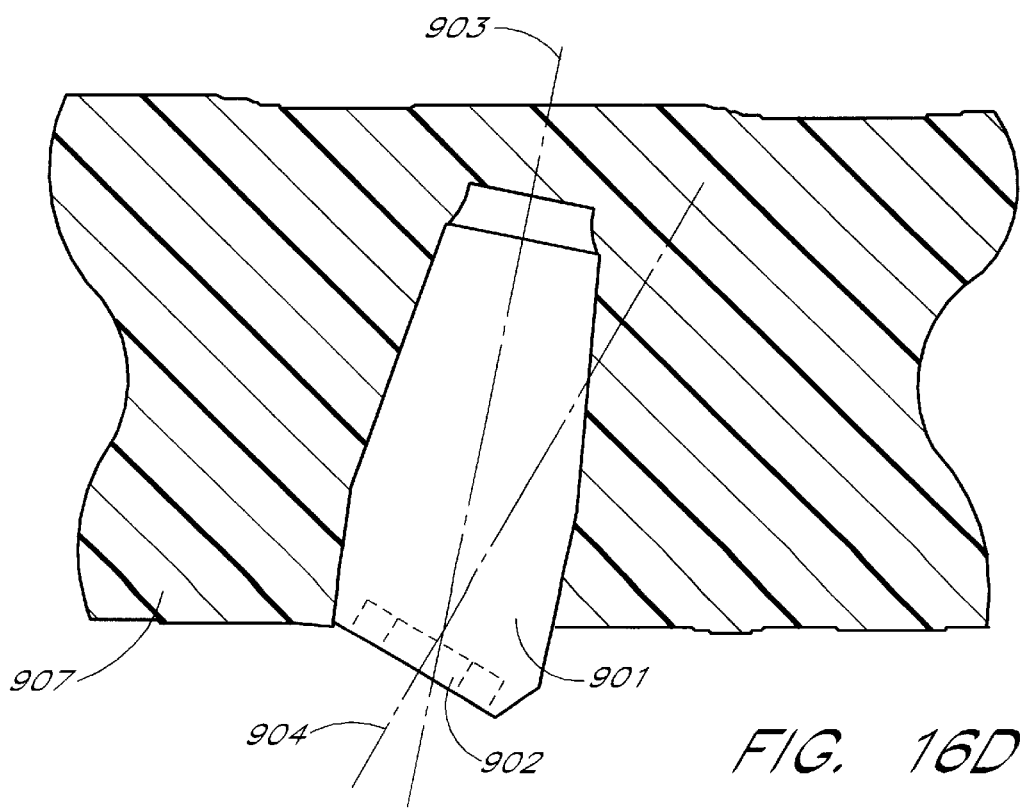
FIG. 16D is a schematic illustration of the impression material illustrated in FIG. 16C in which the multi-orientation impression coping of FIG. 16A has been reinserted.

Second, to the extent that the longitudinal axis of the hexagonal recessed area is not precisely parallel to and collinear with the longitudinal axis of the body of the impression coping, inaccuracies will occur in the construction of the plaster analogue whenever the impression coping is reinserted into the impression material in an indexed orientation different from the original indexed orientation. The source of this inherent inaccuracy in multiple-orientation impression copings can be demonstrated by reference to FIGS. 16A–16D. FIG. 16A illustrates an impression coping 900 in which the longitudinal axis 904 of the hexagonal recessed area 902 is not precisely parallel to the longitudinal axis 903 of the body 901 of the impression coping 900. As shown in FIG. 16B, when the impression coping 900 of FIG. 16A is situated over an implant fixture 905, the longitudinal axis 903 of the body 901 points slightly away from the collinear longitudinal axes of the hexagonal recessed area 902 and the implant fixture 905. Referring to FIG. 16C, when an impression is taken of the impression coping 900 as positioned in FIG. 16B, an impression 906 is made in impression material 907. The impression 906 has a longitudinal axis 908, which also points slightly away from the direction of the longitudinal axis of the implant fixture 905. When the impression coping 900 is reinserted into the impression material 907 in an indexed orientation different from its original orientation, as shown in FIG. 16D, the longitudinal axis 903 of the body 901 will be collinear with the longitudinal axis 908 of the impression 906, but the direction of the longitudinal axis 904 of the hexagonal recessed area 902 will not be collinear with the longitudinal axis passing through the implant fixture 905. Rather, the longitudinal axis 904 of the hexagonal recessed area 902 will point at an even sharper angle away from the axis of the implant fixture 905. As a result, the plaster analogue will communicate inaccurate information regarding the orientation of the implant fixture in the patient's mouth. Again, in order to minimize the inherent inaccuracies in a self-indexing coping due to this possible "tilt" of the body of the impression coping relative to the recessed area, strict tolerances must be maintained during the manufacturing process, which, again, increases the expense of making multiple-orientation impression copings.

The impression coping of the present invention is less expensive to manufacture than multiple-orientation impression copings because it does not require such strict range of tolerances. Any inherent inaccuracies in the single-orientation impression coping of the present invention, if transferred to the impression material, will be reversed when making the plaster analogue because there is only one possible orientation of the impression coping.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A universal impression coping system for use in taking an accurate dental impression of an implant installed in patient's jawbone using either a closed-tray or open-tray impression technique, comprising:

an impression pin, including a body portion having a proximal end and a distal end, said proximal end being configured and adapted to be secured to said implant and further comprising an indexing boss or recess formed therein for interlockingly engaging a corresponding mating indexing boss or recess formed on said implant, said impression pin having a central bore extending substantially completely through said impression pin and opening through said proximal and distal ends;

a cap screw having a cap portion and a threaded shaft portion, said threaded shaft portion being adapted to pass through said bore extending through said impression pin and to threadingly engage a threaded bore of said implant, said cap portion being adapted to selectively matingly engage or abut against the distal end of said impression pin; and an embedment cap having one or more impression gripping elements and being adapted to selectively matingly engage or abut against the distal end of said impression pin, said embedment cap having a central bore extending substantially therethrough;

whereby said cap screw may be selectively engaged or abutted to said impression pin for use in a closed-tray impression technique and whereby said embedment cap may be selectively engaged or abutted to said impression pin for use in an open-tray impression technique.

2. The universal impression coping of claim 1 further comprising a bolt or screw having a head portion and a threaded shaft portion, said bolt or screw being sized and adapted to pass through said bore extending through said embedment cap and through said bore extending through said impression pin and to threadingly engage said threaded bore of said implant.

3. The universal impression coping of claim 1 wherein said body portion of said impression pin is tapered such that the proximal end is generally wider than the distal end.

4. The universal impression coping of claim 1 wherein said body portion further includes one or more longitudinal key-ways.

5. The universal impression coping of claim 4 wherein said key ways are defined by a pair of planar surfaces at substantially right angles with one another and defining a dove tail key therebetween.

6. The universal impression coping of claim 1 wherein said body portion of said impression pin further includes a waist portion extending at least part way around said impression pin body portion.

7. A method of using the universal impression coping system of claim 1, comprising the steps of:
   examining an implant site and selecting between open-tray and closed-tray dental impression techniques;
   if a closed tray impression technique is selected, engaging said cap screw to said impression pin, securing said cap screw and said impression pin to an implant and taking said impression; and
   if an open-tray is selected, engaging said embedment cap to said impression pin and securing said impression pin and said embedment cap to said implant and taking said impression.

8. The method of claim 7 wherein the securing said impression pin and said embedment cap to said implant step includes passing a threaded shaft portion of a bolt or screw through a central bore of said embedment cap and engaging said threaded shaft portion with a threaded bore of said implant.

9. The method of claim 8 further comprising, if an open tray impression technique is selected, the step of releasing said impression pin and said embedment cap from said implant after taking said impression.

10. The method of claim 9 wherein the releasing said impression pin and said embedment cap step includes unthreading said threaded bolt portion of said bolt or screw from said threaded bore of said implant.

11. The pick-up impression coping of claim 1 wherein said gripping elements comprise a pair of generally square plates.

12. The pick-up impression coping of claim 11 wherein said pair of generally square plates are rotated axially approximately 45 degrees relative to each other.

13. The pick-up impression coping of claim 1 wherein said embedment cap includes a lower portion configured to fit within said bore extending through said impression pin.

14. The pick-up impression coping of claim 13 wherein said lower portion of said embedment cap is adapted to frictionally engage an inner surface of said bore extending through said impression pin.

15. The pick-up impression coping of claim 14 wherein said lower portion of said embedment cap includes at least two flexible fingers.

16. A transfer impression coping for use in taking an accurate dental impression of an implant installed in patient's jawbone, comprising:
   an impression pin, including a body portion having a proximal end and a distal end, said proximal end being configured and adapted to be secured to said implant and further comprising an indexing boss or recess formed therein for interlockingly engaging a corresponding mating indexing boss or recess formed on said implant, said impression pin having a central bore extending substantially completely through said impression pin and opening through said proximal and distal ends, said body portion further includes one or more longitudinal key-ways wherein said keyways are defined by a pair of planar surfaces at substantially right angles with one another and defining a dove tail key therebweteen; and
   a cap screw having a cap portion and a threaded shaft portion, said threaded shaft portion being adapted to pass through said bore extending through said impression pin and to threadingly engage a threaded bore of said implant, said cap portion being adapted to selectively matingly engage or abut against the distal end of said impression pin.

17. The transfer impression coping of claim 16 wherein said body portion of said impression pin is tapered such that the proximal end is generally wider than the distal end.

18. The transfer impression coping of claim 16 wherein said body portion of said impression pin further includes a waist portion extending at least part way around said impression pin body portion.

19. A pick-up impression coping for use in taking an accurate dental impression of an implant installed in patient's jawbone, comprising:
   an impression pin, including a body portion having a proximal end and a distal end, said proximal end being configured and adapted to be secured to said implant and further comprising an indexing boss or recess formed therein for interlockingly engaging a corresponding mating indexing boss or recess formed on said implant, said impression pin having a central bore extending substantially completely through said impression pin and opening through said proximal and distal ends;
   an embedment cap having one or more impression gripping elements and being adapted to selectively matingly engage or abut against the distal end of said impression pin, said embedment cap having a central bore extending substantially therethrough; and
   a bolt or screw having a head portion and a threaded shaft portion, said bolt or screw being sized and adapted to pass through said bore extending through said embedment cap and through said bore extending through said impression pin and to threadingly engage said threaded bore of said implant.

20. The pick-up impression coping of claim 19 wherein said body portion of said impression pin is tapered such that the proximal end is generally wider than the distal end.

21. The pick-up impression coping of claim 19 wherein said body portion of said impression pin further includes a waist portion extending at least part way around said impression pin body portion.

22. The pick-up impression coping of claim 19 wherein said gripping elements comprise a pair of generally square plates.

23. The pick-up impression coping of claim 22 wherein said pair of generally square plates are rotated axially approximately 45 degrees relative to each other.

24. The pick-up impression coping of claim 19 wherein said embedment cap includes a lower portion configured to fit within said bore extending through said impression pin.

25. The pick-up impression coping of claim 24 wherein said lower portion of said embedment cap is adapted to frictionally engage an inner surface of said bore extending through said impression pin.

26. The pick-up impression coping of claim 24 wherein said lower portion of said embedment cap includes at least two flexible fingers.

27. The pick-up impression coping of claim 19 wherein said body portion further includes one or more longitudinal key-ways.

28. The pick-up impression coping of claim 27 wherein said keyways are defined by a pair of planar surfaces at substantially right angles with one another and defining a dove tail key therebweteen.

29. A pick-up impression coping for use in taking an accurate dental impression of an implant installed in patient's jawbone, comprising:

- an impression pin, including a body portion having a proximal end, a distal end and a longitudinal axis extending between said proximal end and said distal end, said proximal end being configured and adapted to be secured to said implant and further comprising an indexing boss or recess formed therein for interlockingly engaging a corresponding mating indexing boss or recess formed on said implant, said impression pin having a central bore extending substantially completely through said impression pin and opening through said proximal and distal ends;
- an embedment cap having a retention surface that lies transverse to the longitudinal axis, said embedment cap and being adapted to selectively matingly engage or abut against the distal end of said impression pin and having a central bore extending substantially therethrough; and
- a bolt or screw having a head portion and a threaded shaft portion, said bolt or screw being sized and adapted to pass through said bore extending through said embedment cap and through said bore extending through said impression pin and to threadingly engage said threaded bore of said implant.

30. The pick-up impression coping of claim 29 wherein said body portion of said impression pin is tapered such that the proximal end is generally wider than the distal end.

31. The pick-up impression coping of claim 29 wherein said body portion further includes one or more longitudinal key-ways.

32. The pick-up impression coping of claim 31 wherein said keyways are defined by a pair of planar surfaces at substantially right angles with one another and defining a dove tail key therebweteen.

33. The pick-up impression coping of claim 29 wherein said body portion of said impression pin further includes a waist portion extending at least part way around said impression pin body portion.

34. The pick-up impression coping of claim 29 wherein said retention surface is defined, at least in part, by a pair of generally square plates.

35. The pick-up impression coping of claim 34 wherein said pair of generally square plates are rotated axially approximately 45 degrees relative to each other.

36. The pick-up impression coping of claim 29 wherein said embedment cap includes a lower portion configured to fit within said bore extending through said impression pin.

37. The pick-up impression coping of claim 36 wherein said lower portion of said embedment cap is adapted to frictionally engage an inner surface of said bore extending through said impression pin.

38. The pick-up impression coping of claim 36 wherein said lower portion of said embedment cap includes at least two flexible fingers.

\* \* \* \* \*